(12) United States Patent
Gygi et al.

(10) Patent No.: US 7,332,613 B2
(45) Date of Patent: Feb. 19, 2008

(54) CAPTURE AND RELEASE BASED ISOTOPE TAGGED PEPTIDES AND METHODS FOR USING THE SAME

(75) Inventors: Steven P. Gygi, Foxboro, MA (US); Scott Anthony Gerber, Brookline, MA (US); Carlos Augusto Gartner, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 147 days.

(21) Appl. No.: 10/863,589

(22) Filed: Jun. 7, 2004

(65) Prior Publication Data
US 2004/0259164 A1    Dec. 23, 2004

Related U.S. Application Data

(60) Provisional application No. 60/476,511, filed on Jun. 6, 2003.

(51) Int. Cl.
*C07D 235/02*    (2006.01)

(52) U.S. Cl. ............... 548/303.7; 548/304.1; 530/345; 435/7.5; 436/173

(58) Field of Classification Search ............ 548/303.7, 548/304.1; 435/7.5; 530/345; 436/173
See application file for complete search history.

(56) References Cited

U.S. PATENT DOCUMENTS 5,391,711 A  *  2/1995  Funakoshi et al. .......... 530/344
6,156,527 A     12/2000 Schmidt et al.
6,287,792 B1     9/2001  Pardridge et al.
6,629,040 B1     9/2003  Goodlett et al.
6,670,194 B1    12/2003  Aebersold et al.

FOREIGN PATENT DOCUMENTS

WO    WO 00/11208    3/2000

OTHER PUBLICATIONS

Hsu, Joseph C. (Plant and Cell Physiology 13(4), 689-94, 1972).*
Schulze E (Comparative biochemistry and physiology. B, Comparative Biochemistry 103(4), 913-6, 1992).*
Bender, Margaret M. (Phytochemistry (Elsevier) 10(6), 1239-44, 1971).*
Gaffney J. S. (Biomedical Mass Spectrometry 5(8), 495-7, 1978).*
Ritter (Chem Eng News 84, 43-45, 2006).*
Welte, Dietrich H. (Naturwissenschaften 56(3), 133-4, 1969).*

* cited by examiner

*Primary Examiner*—David Lukton
(74) *Attorney, Agent, or Firm*—George W. Neuner; Jonathan M. Sparks; Edwards Angell Palmer & Dodge LLP

(57) ABSTRACT

The invention provides non-affinity based isotope tagged peptides, chemistries for making these peptides, and methods for using these peptides. In one aspect, tags comprise a reactive site (RS) for reacting with a molecule on a protein to form a stable association with the peptide (e.g., a covalent bond) and an anchoring site (AS) group for reversibly or removably anchoring the tag to a solid phase such as a resin support. Anchoring may be direct or indirect (e.g., through a linker molecule). Preferably, the anchoring site comprises a biotin compound. Preferably, the tag comprises a mass-altering label, such as a stable isotope, such that association of the tag with the peptide can be monitored by mass spectrometry. The reagents can be used for rapid and quantitative analysis of proteins or protein function in mixtures of proteins.

19 Claims, 14 Drawing Sheets

Examples of Cleavable Linkers

Si-Carbon cleavages

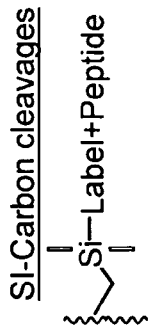

(where "Label" is aryl)

Cleaved by Br, I, DMF/DMSO+$H_2O$ and heat

Nucleophilic cleavages

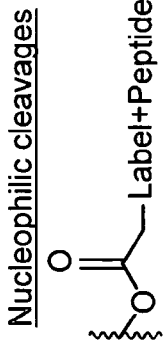

Cleaved by nucleophiles
(e.g. hydrazine, ethlyamine, etc.)

Redox cleavages

S Cleaved by oxidizing or reducing agents
(e.g. BME, DTT, DMSO/ Heat, etc.)

Photochemical cleavages

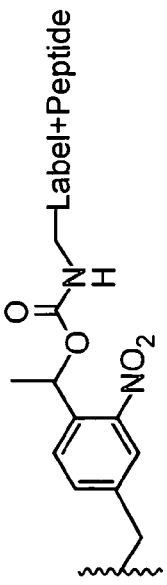

Cleaved by irradiation

Enzymatic cleavages

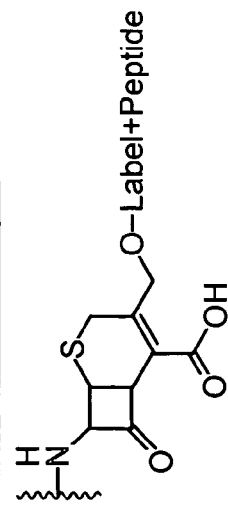

Cleaved by substrate-specific enzymes
(e.g. beta-lactamase, glycosiases, lipases, etc.)

Label = $^{13}C$, $^{15}N$, $^{2}H$, etc. on alkyl, aryl, etc.

FIG. 2

Two Strategies For Capturing And Labelling Cysteine-Containing Peptides

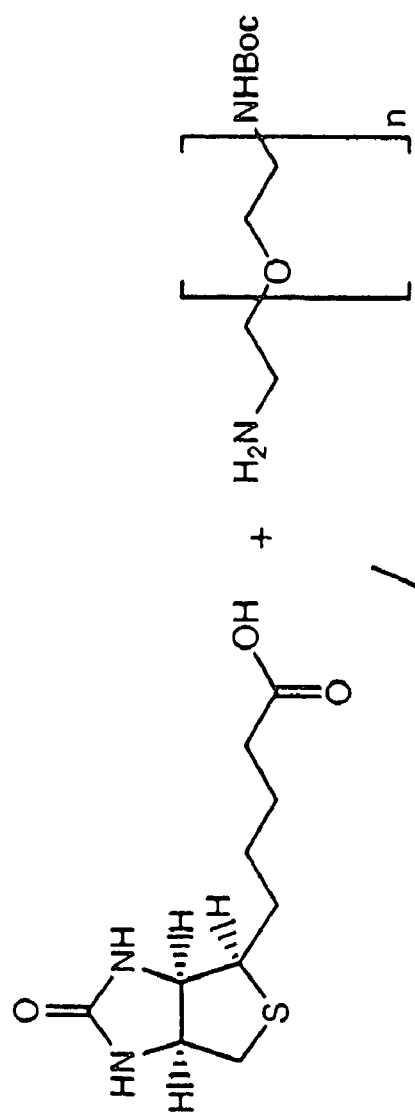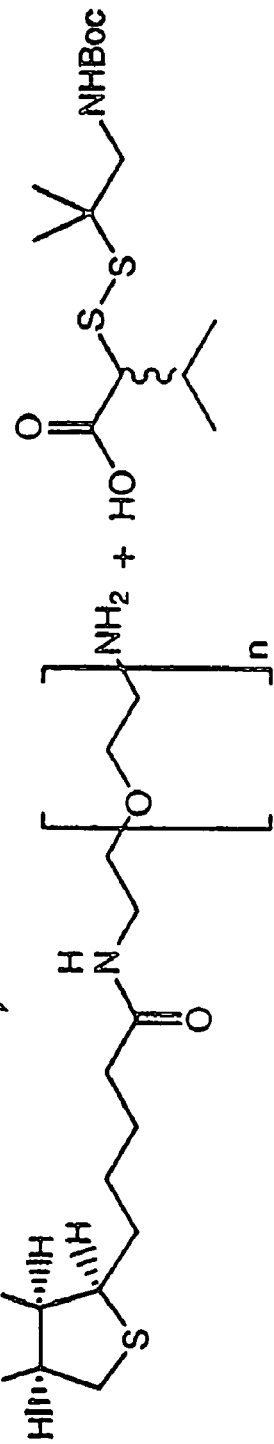
FIG. 6A

ESGSLSPEHGPVVVHCSAGIGR
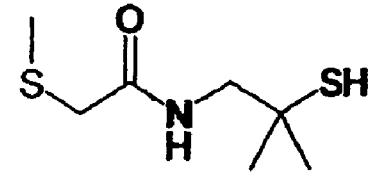
145
ESGSLSPEHGPVVVHCSAGIGR
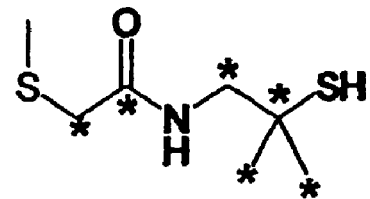
151
*=Carbon-13 atom
FIG. 16B

SEQUENCE LISTING

<160> NUMBER OF SEQ ID NOS: 1

<210> SEQ ID NO 1
<211> LENGTH: 22
<212> TYPE: PRT
<213> ORGANISM: Homo sapiens

```
<400> SEQUENCE: 1

Glu Ser Gly Ser Leu Ser Pro Glu His Gly Pro Val Val Val His Cys
 1               5                  10                  15

Ser Ala Gly Ile Gly Arg
            20
```

CAPTURE AND RELEASE BASED ISOTOPE TAGGED PEPTIDES AND METHODS FOR USING THE SAME

RELATED APPLICATIONS

This application claims priority under 35 U.S.C. §119(e) to No. 60/476,511 filed Jun. 6, 2003, the entirety of which is hereby incorporated by reference.

GOVERNMENT GRANTS

At least part of the work contained in this application was performed under government grant HG00041 from the National Institutes of Health. The government may have certain rights in this invention.

FIELD OF THE INVENTION

The invention relates to stable isotope tags and methods of using these for quantitative protein expression profiling.

BACKGROUND OF THE INVENTION

Proteins are essential for the control and execution of virtually every biological process. Protein function is not necessarily a direct manifestation of the expression level of a corresponding mRNA transcript in a cell, but is impacted by post-translational modifications, such as protein phosphorylation, and the association of proteins with other biomolecules. It is therefore essential that a complete description of a biological system include measurements that indicate the identity, quantity and the state of activity of the proteins which constitute the system. The large-scale analysis of proteins expressed in a cell or tissue has been termed proteome analysis (Pennington et al., 1997).

At present no protein analytical technology approaches the throughput and level of automation of genomic technology. The most common implementation of proteome analysis is based on the separation of complex protein samples, most commonly by two-dimensional gel electrophoresis (2DE), and the subsequent sequential identification of the separated protein species (Ducret et al., 1998; Garrels et al., 1997; Link et al., 1997; Shevchenko et al., 1996; Gygi et al. 1999; Boucherie et al., 1996). This approach has been revolutionized by the development of powerful mass spectrometric techniques and the development of computer algorithms which correlate protein and peptide mass spectral data with sequence databases and thus rapidly and conclusively identify proteins (Eng et al., 1994; Mann and Wilm, 1994; Yates et al., 1995).

This technology has reached a level of sensitivity which now permits the identification of essentially any protein which is detectable by conventional protein staining methods including silver staining (Figeys and Aebersold, 1998; Figeys et al., 1996; Figeys et al., 1997; Shevchenko et al., 1996). However, the sequential manner in which samples are processed limits the sample throughput, the most sensitive methods have been difficult to automate and low abundance proteins, such as regulatory proteins, escape detection without prior enrichment, thus effectively limiting the dynamic range of the technique.

The development of methods and instrumentation for automated, data-dependent electrospray ionization (ESI) tandem mass spectrometry (MS/MS) in conjunction with microcapillary liquid chromatography (LC) and database searching has significantly increased the sensitivity and speed of the identification of gel-separated proteins. Microcapillary LC-MS/MS has been used successfully for the large-scale identification of individual proteins directly from mixtures without gel electrophoretic separation (Link et al., 1999; Opitek et al., 1997). However, while these approaches dramatically accelerate protein identification, quantities of the analyzed proteins cannot be easily determined, and these methods have not been shown to substantially alleviate the dynamic range problem also encountered by the 2DE/MS/MS approach. Therefore, low abundance proteins in complex samples are also difficult to analyze by the microcapillary LC/MS/MS method without their prior enrichment.

There is thus a need to provide methods for the accurate comparison of protein expression levels between cells in two different states, particularly for comparison of low abundance proteins. ICAT™ reagent technology makes use of a class of chemical reagents called isotope coded affinity tags (ICAT). These reagents exist in isotopically heavy and light forms which are chemically identical with the exception of eight deuterium or hydrogen atoms, respectively. Proteins from two cells lysates can be labeled independently with one or the other ICAT reagent at cysteinyl residues. After mixing and proteolysing the lysates, the ICAT-labeled peptides are isolated by affinity to a biotin molecule incorporated into each ICAT reagent. ICAT-labeled peptides are analyzed by LC-MS/MS where they elute as heavy and light pairs of peptides. Quantification is performed by determining the relative expression ratio relating to the amount of each ICAT-labeled peptide pair in the sample.

Identification of each ICAT-labeled peptide is performed by a second stage of mass spectrometry (MS/MS) and sequence database searching. The end result is relative protein expression ratios on a large scale. The major drawback to this technique are 1) quantification is only relative; 2) specialized chemistry is required, and 3) database searches are hindered by the presence of the large ICAT reagent molecule, and 4) relative amounts of posttranslationally modified (e.g., phosphorylated) proteins are transparent to analysis.

SUMMARY OF THE INVENTION

The present invention provides improved chemistry, reagents, and kits for accurate quantification of proteins. In one preferred aspect, proteins can be quantitated directly from cell lysates. The reagents can be used for the rapid and quantitative analysis of protein in mixtures of proteins, e.g., to profile the proteome of a cell at a particular cell state.

In another aspect, the invention provides a reagent for mass spectrometric analysis of proteins comprising a tag molecule. Preferably, the tag molecule comprises a reactive site for stably associating with a protein, an isotope label, and an anchoring site for anchoring the tag molecule to a solid phase. Anchoring may be direct, e.g., as a consequence of a covalent or non-covalent bond between the anchoring site of the tag and the solid phase, or indirect, through a linker which can be cleaved from the tag molecule.

A particularly useful anchoring site is provided by biotin, which is well known to complex with avidin. A series of new biotin based catch and release reagents are provided by the invention which comprise a biotin residue and alkylating group which are connected by a linker. Preferred alkylating groups are suitable for alkylating cysteine residues of polypeptides. Preferred Biotin derivatives comprise biotin and a 2-[2-(2-iodo-acetylamino)-1,1-dimethyl-ethyldisulfanyl]-3-methyl-butyric acid coupled through a di(2-aminoethyl)ether, which may have one or more ethylene glycol repeat units interposed between the amino residues, e.g., a linker of the formula: —NH((CH$_2$)$_2$O)$_n$(CH$_2$)$_2$NH—, where n is an integer of from 0 to about 5.

When using biotin derivatives in accord with the present invention, the tag portion of the reagent is cleavable by pH, or a reducing agent, or other means, but not by reversing the affinity bond between the biotin and avidin. Thus, although affinity complexing is utilized to attach to the solid phase, the cleavable bond is other than the affinity bond. Preferably, the cleavable bond to disassociate the tag is capable of cleaving by a reducing agent. More preferably, the bond cannot be cleaved by a free disulfide, but is cleaved by a phosphine reducing agent such as TCEP or the like.

In another preferred aspect, the anchoring site of the tag molecule forms a pH sensitive bond with the solid phase. Preferably, the anchoring site forms covalent bonds to a cis hydroxyl pair on the solid phase under selected pH and reducing conditions and can be disassociated from the solid phase by changing those conditions. Particularly preferred are bonds that are sterically hindered such that they are not cleaved by free dissulfides but are cleaved by phosphines.

In another aspect, the tag molecule comprises the general formula R—B(OH$_2$), wherein the R group is a suitable chemical moiety for attaching the isotope. Suitable R groups include, but are not limited to: an alkyl group, aryl group, heteroaryl group, arylalkyl group, heteroarylalkyl group, and a cyclic molecule. In a further aspect, the tag molecule is phenyl-B(OH)$_2$.

Preferred isotopes are stable isotopes selected from the group consisting of a stable isotope of hydrogen, nitrogen, oxygen, carbon, phosphorous and sulfur.

Reactive site groups include, but are not limited to chemical moieties that react with sulfhydryl groups, amino groups, carboxylate groups, ester groups, phosphate groups, aldehyde groups, ketone groups and with homoserine lactone after fragmentation with CNBr. Sites on proteins may be naturally reactive with reactive site groups or can be made reactive upon exposure to an agent (e.g., an alkylating agent, a reducing agent, etc).

In one aspect, the reactive site group of the tag molecule forms a stable association with a modified residue of a protein. The modified residue may be glycosylated, methylated, acylated, phosphorylated, ubiquinated, farnesylated, or ribosylated.

The pH sensitive anchoring group of a tag molecule forms a bond with a solid phase under selected pH and reducing conditions. Examples of sensitive bonds include, but are not limited to: acyloxyalkyl ether bonds, acetal bonds, thioacetal bonds, aminal bonds, imine bonds, carbonate bonds, and ketal bonds. Preferred bonds are the disulfide bonds.

The invention also provides a composition comprising a pair of tag molecules as described above, where each member of the pair is identical except for the mass of the isotope attached thereto. For example, one member of the pair comprises a heavy isotope and the other member of the pair comprises the corresponding light form of the isotope. Alternatively, one member of the pair may be labeled while the other member is not.

The invention further provides a kit comprising reagents and/or compositions as described above, and one or more of a reagent selected from the group consisting of: an activating agent for providing active groups on a protein which bind to the reactive site of the tag molecule; a solid phase; one or more agents for lysing a cell; a pH controlling agent; a reducing agent; one or more proteases; one or more cell samples or fractions thereof. The tag molecule may further be stably associated with a peptide. A preferred class of reducing agents are the phosphines, e.g., TCEP.

Kits of the invention for use of a biotin based reagent preferably also contain a biotin derivative comprising biotin and a 2-[2-(2-iodo-acetylamino)-1,1-dimethyl-ethyldisulfanyl]-3-methyl-butyric acid coupled through a di(2-aminoethyl)ether, which may have one or more ethylene glycol repeat units interposed between the amino residues, e.g., a linker of the formula: —NH((CH$_2$)$_2$O)$_n$(CH$_2$)$_2$NH—, where n is an integer of from 0 to about 5.

The invention also provides kits comprising a plurality of tagged peptide molecules, each tagged peptide molecule comprising a peptide and a tag molecule stably associated with the protein, the tag molecule further comprising an isotope label, and a reducing agent sensitive anchoring site for anchoring the tag molecule to a solid phase. In one aspect, the kit comprises pairs of tagged peptides and each member of a pair of tagged peptides comprises an identical peptide and is differentially labeled from the other member of the pair. In another aspect, the kit comprises at least one set of tagged peptides, the set comprising different peptides corresponding to a single protein. In still another aspect, at least one set of tagged peptides comprises peptides corresponding to modified and unmodified forms of a single protein. In a further aspect, the kit comprises at least one set of tagged peptides from a first cell at a first cell state and at least one set of tagged peptides from a second cell at a second cell state. For example, the first cell may be a normally proliferating cell while the second cell is an abnormally proliferating cell (e.g., a cancer cell). First and second cells may also represent different stages of cancer.

The invention additionally provides a method for identifying one or more proteins or protein functions in one or more samples containing mixtures of proteins. In one aspect, the method comprises: reacting a first sample with any of the reagents described above and a solid phase under conditions suitable to form a solid phase-isotope labeled tag molecule-protein complex. The complex is exposed to one or more proteases, generating solid phase-isotope labeled tag molecule-peptide complexes and untagged peptides. The solid phase-isotope labeled tag molecule-peptide complexes are purified from untagged peptides and exposed to a reducing agent which disrupts associations between the anchoring site of the tag molecule and the solid phase, thereby releasing tagged peptides from the solid phase. Preferably, the sample is subjected to a separation step such as liquid chromatography. The mass of the tagged peptide is determined and correlated with the identity and/or activity of a protein (e.g., the presence of a particular modified form of a protein which is known to be active). Preferably, a mass-to-charge ratio is determined, e.g., by multistage mass spectrometric (MS$^n$) analysis. In addition to determining the identity of a protein, a quantitative measure of the amount of protein in the sample may be obtained. The method may also be used to determine the site of a modification of a protein in one or more samples, by reacting sample proteins with a tag molecule comprising a reactive site which reacts with a modified residue on the protein. In another aspect, the amount of a modified protein in a sample is also determined.

In a further aspect, the method further comprises reacting a second sample with a second reagent comprising an identical molecular tag as the reagent used in the first sample but which is differentially labeled. Samples are processed in parallel and combined prior to protease digestion. This generates a combined sample comprising at least one pair of tagged peptides, each member of the pair comprising identical peptides but differing in mass. The ratio of members of at least one tagged peptide pair in the combined sample is determined. Preferably, mass spectra are generated. Such spectra will comprise at least one signal doublet for each peptide in the sample, the signal doublet comprising a first signal and a second signal shifted a number of known units from the first signal. The known units will represent the difference in molecular weight between the two members of a tagged peptide pair. Preferably, a signal ratio for a given peptide is determined by relating the difference in signal intensity between the first signal and the second signal.

The relative amounts of members of a tagged peptide pair in the two samples are determined and correlated with the abundance the protein corresponding to the peptide in the sample. Abundance may be correlated with the state of cells from which the samples were obtained. The correlation may be used to diagnose a pathological condition in a patient from whom one of the cell samples was obtained (e.g., where one of the cell states represent a disease condition).

Single samples or multiple samples may be analyzed by relating mass spectra data from a tagged peptide to an amino acid sequence. The steps of the method can be repeated, either sequentially or simultaneously, until substantially all of the proteins in a sample are detected and/or identified. In this way a proteome profile for one or more cells can be obtained.

BRIEF DESCRIPTION OF THE FIGURES

The objects and features of the invention can be better understood with reference to the following detailed description and accompanying drawings.

FIG. 2 shows exemplary cleavable linkers that can be used in the method shown in FIG. 1.

FIG. 5A shows the use of a boron-based molecular tag which binds to a resin support comprising cis hydroxy groups presented by a 5-membered cyclic ring compound via the two hydroxy groups on the tag. The tag binds to proteins via a cysteine reactive moiety.

FIG. 16B illustrates a tagged protein (SEQ ID NO: 1) after cleavage from the reagent at the disulfide bond for tag and $C^{13}$ labeled tag.

DETAILED DESCRIPTION OF THE INVENTION

Figure 1:
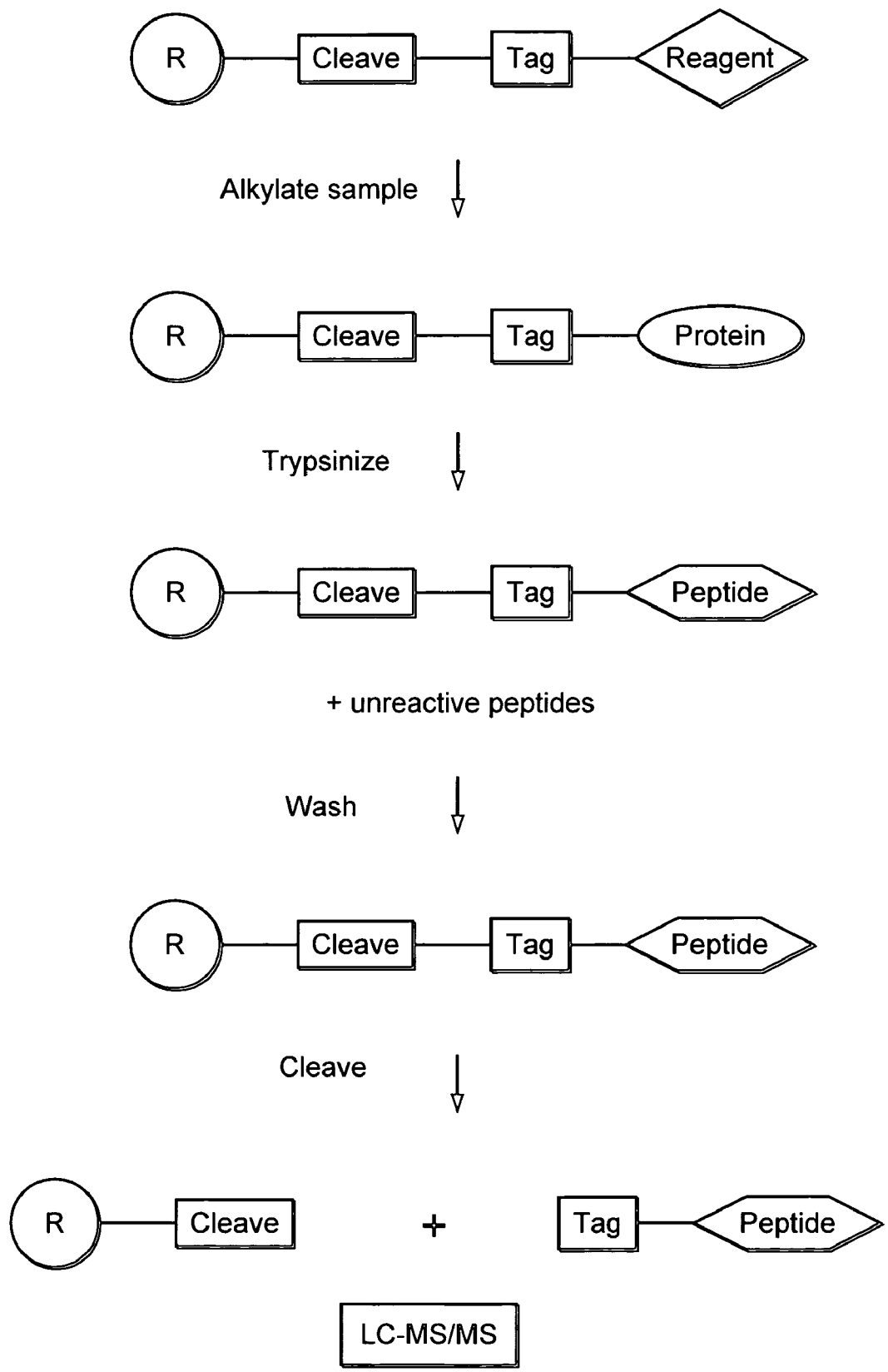
FIG. 1 is a schematic diagram illustrating the use of resin-based chemistries to tag peptides according to one aspect of the invention.
Figure 3:
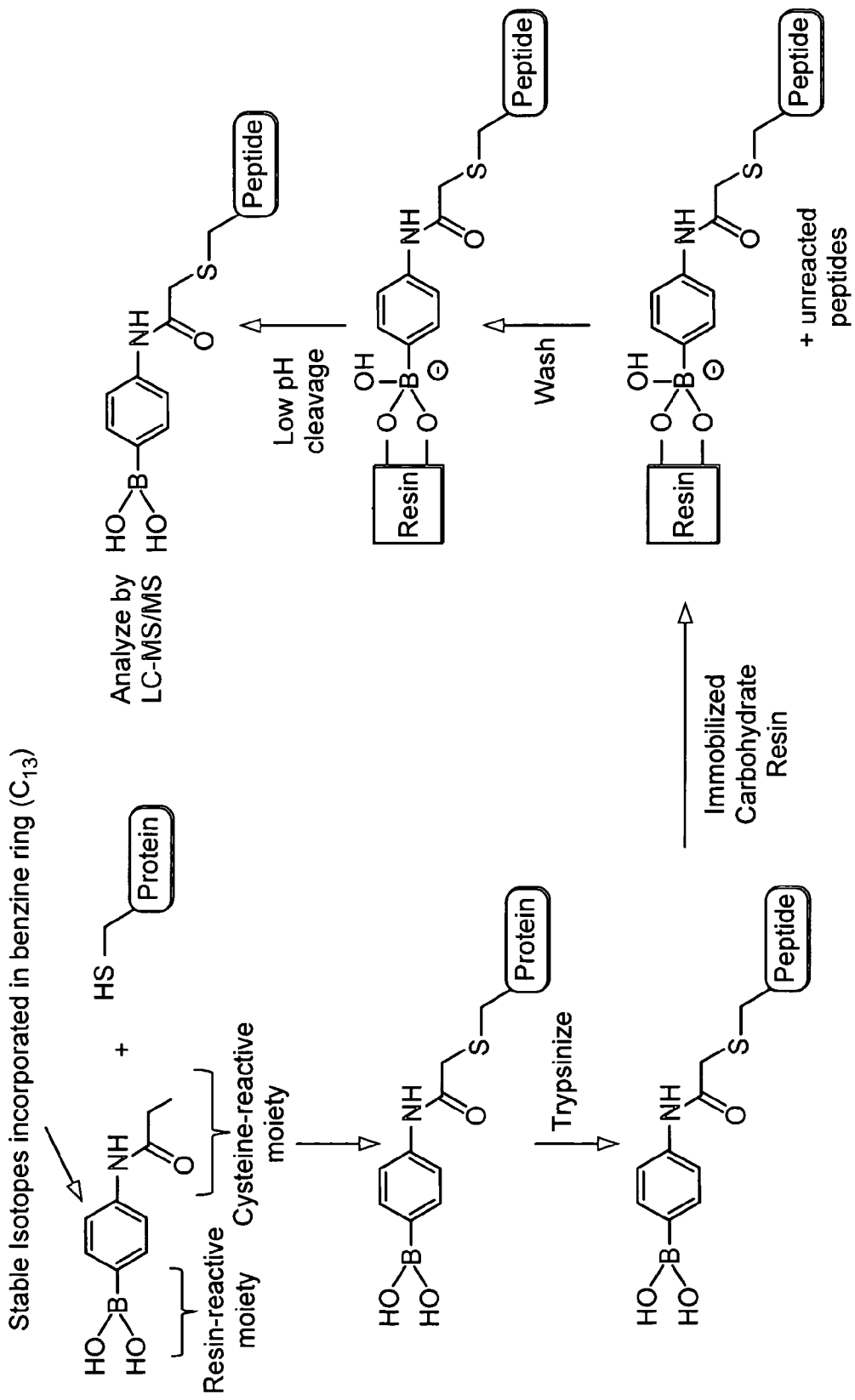
FIG. 3 shows the use of arylboronic acids for protein quantification according to one aspect of the invention.

The invention provides non-affinity based isotope tagged peptides, chemistries for making these peptides, and methods for using these peptides. In one aspect, tags comprise a reactive site (RS) for reacting with a molecule on a protein to form a stable association with the peptide (e.g., a covalent bond) and an anchoring site (AS) group for reversibly or removably anchoring the tag to a solid phase such as a resin support. Anchoring may be direct or indirect (e.g., through a linker molecule). Preferably, the tag comprises a mass-altering label, such as a stable isotope, such that association of the tag with the peptide can be monitored by mass spectrometry. The reagents can be used for rapid and quantitative analysis of proteins or protein function in mixtures of proteins.

Definitions

The following definitions are provided for specific terms which are used in the following written description.

As used in the specification and claims, the singular form "a", "an" and "the" include plural references unless the context clearly dictates otherwise. For example, the term "a cell" includes a plurality of cells, including mixtures thereof. The term "a protein" includes a plurality of proteins.

"Protein", as used herein, means any protein, including, but not limited to peptides, enzymes, glycoproteins, hormones, receptors, antigens, antibodies, growth factors, etc., without limitation. Presently preferred proteins include those comprised of at least 25 amino acid residues, more preferably at least 35 amino acid residues and still more preferably at least 50 amino acid residues.

As used herein, the term "peptide" refers to a compound of two or more subunit amino acids. The subunits are linked by peptide bonds.

As used herein, the term "alkyl" refers to univalent groups derived from alkanes by removal of a hydrogen atom from any carbon atom: $C_nH_{2n+1}$—. The groups derived by removal of a hydrogen atom from a terminal carbon atom of unbranched alkanes form a subclass of normal alkyl (n-alkyl) groups: $H[CH_2]_n$—. The groups $RCH_2$—, $R_2CH$— (R not equal to H), and $R_3C$— (R not equal to H) are primary, secondary and tertiary alkyl groups respectively. C(1-22)alkyl refers to any alkyl group having from 1 to 22 carbon atoms and includes C(1-6)alkyl, such as methyl, ethyl, propyl, iso-propyl, butyl, pentyl and hexyl and all possible isomers thereof. By "lower alkyl" is meant C(1-6) alkyl, preferably C(1-4)alkyl, more preferably, methyl and ethyl.

As used herein, the terms "aryl" and "heteroaryl" mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S; each of which rings is optionally substituted with 1-3 lower alkyl, substituted alkyl, substituted alkynyl, —NO$_2$, halogen, hydroxy, alkoxy, OCH(COOH)$_2$, cyano, —NZZ, acylamino, phenyl, benzyl, phenoxy, benzyloxy, heteroaryl, or heteroaryloxy; each of said phenyl, benzyl, phenoxy, benzyloxy, heteroaryl, and heteroaryloxy is optionally substituted with 1-3 substituents selected from lower alkyl, alkenyl, alkynyl, halogen, hydroxy, alkoxy, cyano, phenyl, benzyl, benzyloxy, carboxamido, heteroaryl, heteroaryloxy, —NO$_2$ or —NZZ (wherein Z is independently H, lower alkyl or cycloalkyl, and -ZZ may be fused to form a cyclic ring with nitrogen).

"Arylalkyl" means an alkyl residue attached to an aryl ring. Examples are benzyl, phenethyl and the like.

"Heteroarylalkyl" means an alkyl residue attached to a heteroaryl ring. Examples include, e.g., pyridinylmethyl, pyrimidinylethyl and the like.

"Substituted" alkyl groups mean alkyls where up to three H atoms on each C atom therein are replaced with halogen, hydroxy, lower alkoxy, carboxy, carboalkoxy, carboxamido, cyano, carbonyl, —NO$_2$, —NZZ; alkylthio, sulfoxide, sulfone, acylamino, amidino, phenyl, benzyl, heteroaryl, phenoxy, benzyloxy, heteroaryloxy, or substituted phenyl, benzyl, heteroaryl, phenoxy, benzyloxy, or heteroaryloxy.

An "amide" refers to an —C(O)—NH—, where Z is alkyl, aryl, alklyaryl or hydrogen.

A "thioamide" refers to —C(S)—NH-Z, where Z is alkyl, aryl, alklyaryl or hydrogen.

An "ester" refers to an —C(O)—OZ', where Z' is alkyl, aryl, or alklyaryl.

An "amine" refers to a —N(Z')Z", where Z' and Z", is independently hydrogen, alkyl, aryl, or alklyaryl, provided that Z' and Z" are not both hydrogen.

An "ether" refers to Z-O-Z, where Z is either alkyl, aryl, or alkylaryl.

A "thioether" refers to Z-S-Z, where Z is either alkyl, aryl, or alkylaryl.

A "cyclic molecule" is a molecule which has at least one chemical moiety which forms a ring. The ring may contain three atoms or more. The molecule may contain more than one cyclic moiety, the cyclic moieties may be the same or different.

Tag Molecules

Generally, tag molecules according to the invention comprise the formula:

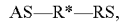

where RS represents a reactive site group for reacting with a protein or peptide, AS represents an anchoring site group for stably associating the tag with a solid phase and R represents the backbone of the tag molecule to which the isotope label (*) is attached. As used herein, "stable" refers to an association which remains intact after extensive and multiple washings with a variety of solutions to remove non-specifically bound components.

The tag can be stably associated with a solid phase (SP) either directly as

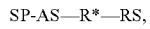

where "—" between SP and AS represents a covalent bond. Preferably, this bond is pH sensitive.

Alternatively, the tag can be stably associated with the solid phase as

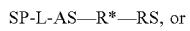

where L is a cleavable linker molecule with at least one cleavage site which can separate the linker from the tag molecule.

Reactive Site Groups

The reactive site of a tag molecule is a group that selectively reacts with certain protein functional groups or is a substrate or cofactor of an enzyme of interest. Preferably, the reactive group of the tag molecule reacts with a plurality of different types of cellular proteins. Reaction of the RS of the tag molecule with functional groups on the protein should occur under conditions that do not lead to substantial degradation of the compounds in the sample to be analyzed. Examples of RS groups include, but are not limited to those which react with sulfhydryl groups to tag proteins containing cysteine, those that react with amino groups, carboxylate groups, ester groups, phosphate reactive groups, and aldehyde and/or ketone reactive groups or, after fragmentation with CNBr, with homoserine lactone.

Cysteine reactive groups include, but are not limited to, epoxides, alpha-haloacyl groups, nitriles, sulfonated alkyl or aryl thiols and maleimides. Amino reactive groups tag amino groups in proteins and include sulfonyl halides, isocyanates, isothiocyanantes, active esters, including tetrafluorophenyl esters, and N-hydroxysuccinimidyl esters, acid halides, and acid anhydrides. In addition, amino reactive groups include aldehydes or ketones in the presence or absence of NaBH$_4$ or NaCNBH$_3$.

Carboxylic acid reactive groups include amines or alcohols which become reactive in the presence of a coupling agent such as dicyclohexylcarbodiimide, or 2,3,5,6-tetrafluorophenyl trifluoroacetate and in the presence or absence of a coupling catalyst such as 4-dimethylaminopyridine; and transition metal-diamine complexes including Cu(II)phenanthroline.

Ester reactive groups include amines which, for example, react with homoserine lactone.

Phosphate reactive groups include chelated metal where the metal is, for example Fe(III) or Ga(III), chelated to, for example, nitrilotriacetiac acid or iminodiacetic acid.

Aldehyde or ketone reactive groups include amine plus NaBH$_4$ or NaCNBH$_3$, or these reagents after first treating a carbohydrate with periodate to generate an aldehyde or ketone.

RS groups can also be substrates for a selected enzyme of interest. The enzyme of interest may, for example, be one that is associated with a disease state or birth defect or one that is routinely assayed for medical purposes. Enzyme substrates of interest for use with the methods of this invention include, acid phosphatase, alkaline phosphatase, alanine aminotransferase, amylase, angiotensin converting enzyme, aspartate aminotransferase, creatine kinase, gamma-glutamyltransferase, lipase, lactate dehydrogenase, and glucose-6-phosphate dehydrogenase which are currently routinely assayed for.

Anchoring Sites

The tags according to the invention further comprise an anchoring site for forming stable associations with a solid phase. Tags are either reversibly anchored (e.g., can associate and dissociate from the solid phase depending on solution conditions, such as pH) or removably anchored (e.g., can be disassociated from the support but unable to reattach under any condition). Stable associations can include covalent or non-covalent bonds and, and as discussed above, may be direct (i.e., the tag may bind covalently or non-covalently to the solid phase) or indirect (i.e., the tag may bind covalently or non-covalently to a linker molecule which itself forms direct stable associations with the solid phase). In this latter scenario, the anchoring site of the tag molecule is the site on the molecule which stably associates with the linker. In one preferred aspect, tags are anchored to solid supports by pH sensitive covalent bonds. In another preferred aspect, tags are anchored to solid supports by bonds cleavable with a reducing agent, preferably a phosphine agent, e.g., TCEP.

Tags according to the invention bind minimally and preferably, not at all, to components in the assay system, except the solid phase, and do not significantly bind to surfaces of reaction vessels. Any non-specific interaction of the affinity tag with other components or surfaces should be disrupted by multiple washes that leave association between the tag and solid phase intact. The tag preferably does not undergo peptide-like fragmentation during $(MS)^n$ analysis. The tag is preferably soluble in the sample liquid to be analyzed even though attached to a solid phase comprising an insoluble resin such as agarose.

The tag molecule preferably also contains groups or moieties that facilitate ionization of tagged peptides. For example, the tag molecule may contain acidic or basic groups, e.g., COOH, $SO_3H$, primary, secondary or tertiary amino groups, nitrogen-heterocycles, ethers, or combinations of these groups. The tag molecule may also contain groups having a permanent charge, e.g., phosphonium groups, quaternary ammonium groups, sulfonium groups, chelated metal ions, tetralky or tetraryl borate or stable carbanions.

Cleavable Linkers

In one aspect, a tag is associated indirectly with a solid phase through a linker molecule. As used herein, a "linker" refers to a bifunctional chemical moiety which comprises an end for stably associating with a solid phase and an end for stably associating with the tag. In one preferred aspect, the linker is cleavable. As used herein, the term "cleavage" refers to a process of releasing a material or compound from a solid support, e.g., to permit analysis of the compound by solution-phase methods. See, e.g., Wells et al. (1998), *J. Org. Chem.* 63:6430-6431.

The linker group should be soluble in the sample liquid to be analyzed and should be stable with respect to chemical reaction, e.g., substantially chemically inert, with respect to components of the sample. Preferably, the linker does not interact with the tag molecule except at the tag molecule's anchoring site and does not interact with the support except at the end of the linker which forms stable associations with the support. Any non-specific interactions of the linker should be broken after multiple washes which leave the solid phase:linker:tag molecule (±peptide) complex intact. Linkers preferably do not undergo peptide-like fragmentation during $(MS)_n$ analysis.

Exemplary linker molecules are shown in FIG. 2. As can be seen from the Figure, the exact chemical structure of the linker can vary to allow cleavage to be controlled in a manner suiting a particular assay format and to allow coupling to a particular tag molecule. Thus, the linker can be cleavable by chemical, thermal or photochemical reaction. Photocleavable groups in the linker may include, but are not limited to, 1-(2-nitrophenyl)-ethyl groups. Thermally labile linkers may include, but are not limited to, a double-stranded duplex formed from two complementary strands of nucleic acid, a strand of a nucleic acid with a complementary strand of a peptide nucleic acid, or two complementary peptide nucleic acid strands which will dissociate upon heating.

Cleavable linkers also include those having disulfide bonds, acid or base labile groups, including among others, diarylmethyl or trimethylarylmethyl groups, silyl ethers, carbamates, oxyesters, ethers, polyethers, diamines, ether diamines, polyether diamines, amides, polyamides, polythioethers, disulfides, silyl ethers, alkyl or alkenyl chains (straight chain or branched and portions of which may be cyclic) aryl, diaryl or alkyl-aryl groups, amides, polyamides, and esters. Enzymatically cleavable linkers include, but are not limited to, protease-sensitive amides or esters, beta-lactamase-sensitive beta-lactam analogs and linkers that are nuclease-cleavable, or glycosidase-cleavable.

Although normally amino acids and oligopeptides are not preferred, when used they typically will employ amino acids of from 2-3 carbon atoms, i.e. glycine and alanine. Aryl groups in linkers can contain one or more heteroatoms (e.g., N, O or S atoms). Linkages also include substituted benzyl ethers, esters, acetals or ketals, diols, and the like (See, U.S. Pat. No. 5,789,172 for a list of useful functionalities and manner of cleavage, herein incorporated by reference). The linkers, when other than a bond, will have from about 1 to 60 atoms, usually 1 to 30 atoms, where the atoms include C, N, O, S, P, etc., particularly C, N and O, and will generally have from about 1 to 12 carbon atoms and from about 0 to 8, usually 0 to 6 heteroatoms. The atoms are exclusive of hydrogen in referring to the number of atoms in a group, unless indicated otherwise.

The series of new biotin based ICAT reagents are provided by the present are particularly useful linkers. These linkers readily form complexes with avidin in solution or attached to a solid phase. As aforesaid, such reagents comprise a biotin residue and alkylating group which are connected by a bond cleavable by a reducing agent without disassociating the biotin side from the solid support. Preferred alkylating groups are suitable for alkylating cysteine residues of polypeptides. Preferred biotin derivatives comprise biotin and a 2-[2-(2-iodo-acetylamino)-1,1-dimethylethyldisulfanyl]-3-methyl-butyric acid coupled through a di(2-aminoethyl)ether, which may have one or more ethylene glycol repeat units interposed between the amino residues, e.g., a linker of the formula: —$NH((CH_2)_2O)_n(CH_2)_2$ NH—, where n is an integer of from 0 to about 5.

Additional types of linker molecules are described in, e.g., Backes and Ellman (1997) *Curr. Opin. Chem. Biol.* 1:86-93, Backes et al. (1996), *J. Amer. Chem. Soc.* 118:3055-3056, Backes and Ellman (1994), *J. Amer. Chem. Soc.* 116:11171-11172, Hoffmann and Frank (1994), *Tetrahedron Lett.* 35:7763-7766, Kocis et al. (1993), *Tetrahedron Lett.* 34:7251-7252, and Plunkett and Ellman (1995), *J. Org. Chem.* 60:6006-6007.

In contrast to affinity-based tag molecules, such as ICAT™ reagents, tag molecules stably associated with linker molecules are generally not displaceable from the solid phase by addition of a displacing ligand or by changing solvent, and the cleavage site of the linker is generally distal from the support and proximal to the tag molecule.

In preferred embodiments of the present invention using biotin derivatives, the affinity complex is used to bind the tag to the solid support but not to release the tag.

pH and Reduction Sensitive Anchoring Sites

In another aspect, the tag comprises a molecule with a pH and/or reduction sensitive anchoring site. Examples of such tags are shown in FIG. 2. In one preferred aspect, such a tag minimally comprises R—B(OH)$_2$), where the R group is a suitable chemical moiety for attaching a label such as a stable isotope. In one embodiment, R is a source of π electrons, i.e., is sp2-bonded to B. Therefore, preferably, R is an aromatic group such as a phenyl molecule. An exemplary tag molecule includes, but is not limited to, phenyl-B (OH)$_2$.

Additionally, the tag molecule comprises an RS group, preferably, covalently bound to the R group and distal from the —OH anchor site groups. In one preferred embodiment, the RS group comprises a cysteine-reactive moiety such as the group shown in FIG. 2. However, generally, any of the RS groups described above may also be used as RS groups.

Additional molecules may present between the RS group and R group; however, preferably, the tag molecule is of a suitable size to facilitate mass spectrometric analysis.

Though boron may be supplied in a variety of ways, it must be present as borate ions in order to bind to a solid phase support (e.g., such as a polysaccharide-containing support). According to D. J. Doonan and L. D. Lower ("Boron Compounds (Oxide, Acids, Borates)", in *Kirk-Othmer Encyclopedia of Chemical Technology*, Vol. 4, p. 67-110, 3rd ed., 1978), boric acid, borate ion and polyions containing various amounts of boron, oxygen, and hydroxyl groups exist in dynamic equilibrium where the percentage of each of the species present is dictated mainly by the pH of the solution. Borate ion begins to dominate the other boron species present in the fluid at a pH of approximately 9.5 and exceeds 95% of total boron species present at a pH of about 11.5. According to B. R. Sanderson ("Coordination Compounds of Boric Acid" in *Mellor's Comprehensive Inorganic Chemistry*, p. 721-764, 1975), boron species (including borate ions and boric acid among others) react with di- and poly-hydroxyl compounds having a cis-hydroxyl pair to form complexes which are in rapid equilibrium with uncomplexed boron species and the cis-hydroxyl compounds. The relative amounts of the complexed and free materials are provided by the equilibrium constants for the specific systems. The equilibrium constants for borate ion is several orders of magnitude larger (typically by factors of $10^4$ to $10^{10}$) than the equilibrium constant for boric acid with the same cis-hydroxyl compound.

For all practical purposes, borate ions form complexes (i.e., can serve to crosslink polysaccharides), while boric acid does not. Therefore, in order to have a useable crosslinked solid phase with the minimum boron content, most of the boron must be present as borate ions which requires a pH of at least about 8.5, preferably at least about 9.5. Reducing pH below these levels will reversibly break covalent bonds between the hydroxyl groups of the borate ions and the solid phase.

Additional tag molecules with pH sensitive anchoring sites include molecules with pH sensitive bonds such as acyloxyalkyl ether, acetal, thioacetal, aminal, imine, carbamate, carbonate, and/or ketal bonds. Solid phases comprising silyl groups additionally can form pH sensitive bonds with hydroxyl, carboxylate, amino, mercapto, or enolizable carbonyl groups on tag molecules.

Particularly useful reduction sensitive bonds are sterically hindered dissulfide bonds, particularly such bonds that are cleavable by a phosphine reducing agent, e.g., TCEP.

In contrast to tag molecules in the art comprising affinity tags (e.g., such as ICAT™ reagents), tag molecules comprising pH and/or reduction sensitive anchoring sites generally retain the functional group that binds to the solid phase when disassociated from the solid phase (e.g., by a change in pH, or by a reducing agent). The smaller size of non-affinity based tag molecules such as those containing boronic acid groups facilitates the analysis of tagged peptides by MS".

Types of Labels

The type of label selected is generally based on the following considerations:

The mass of the label should preferably unique to shift fragment masses produced by MS analysis to regions of the spectrum with low background. The ion mass signature component is the portion of the labeling moiety which preferably exhibits a unique ion mass signature in mass spectrometric analyses. The sum of the masses of the constituent atoms of the label is preferably uniquely different than the fragments of all the possible amino acids. As a result, the labeled amino acids and peptides are readily distinguished from unlabeled amino acids and peptides by their ion/mass pattern in the resulting mass spectrum. In a preferred embodiment, the ion mass signature component imparts a mass to a protein fragment produced during mass spectrometric fragmentation that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions and the labeled tag preferably remains soluble in the MS buffer system of choice. In one aspect, the label increases the ionization efficiency of the protein, or at least does not suppress it. Alternatively or additionally, the label contains a mixture of two or more isotopically distinct species to generate a unique mass spectrometric pattern at each labeled fragment position.

In one preferred aspect, tags comprise mass-altering labels which are stable isotopes. In certain preferred embodiments, the method utilizes isotopes of hydrogen, nitrogen, oxygen, carbon, phosphorous or sulfur. Suitable isotopes include, but are not limited to, $^2$H, $^{13}$C, $^{15}$N, $^{17}$O, $^{18}$O or $^{34}$S. Pairs of tags can be provided, comprising identical tag and peptide portions but distinguishable labels. For example, a pair of tags can comprise isotopically heavy and isotopically light labels, e.g., such as a $^{16}$O:$^{18}$O pair or $^2$H:$^1$H.

Types of Solid Phases

Examples of solid supports suitable for the methods described herein include, but are not limited to: glass supports, plastic supports and the like. These terms are intended to include beads, pellets, disks, fibers, gels, or particles such as cellulose beads, pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, poly-acrylamide beads, latex beads, dimethylacrylamide beads optionally cross-linked with N,N'-bis-acryloyl ethylene diamine, glass particles coated with hydrophobic polymer, and the like, e.g., material having a rigid or semi-rigid surface; and soluble supports such as low molecular weight non-cross-linked polystyrene.

However, in one preferred aspect, the solid phase is a resin. As used herein, a "resin" refers to an insoluble material (e.g., a polymeric material) or particle which allows ready separation from liquid phase materials by filtration. Resins can be used to carry tags and/or tagged peptides. Suitable resins include, but are not limited to, agarose, guaracrylamide, carbohydrate-based polymers (e.g., polysaccharide-containing), and the like.

A "functionalized" solid phase or "functionalized resin" refers to an insoluble, polymeric material or particle comprising active sites for reacting with the anchoring site of a tag molecule allowing anchored tag molecules to be readily separated (by filtration, centrifugation, etc.) from excess reagents, soluble reaction by-products or solvents. See also, Sherrington (1998), *Chem. Commun.* 2275-2286, Winter, In *Combinatorial Peptide and Non-Peptide Libraries* (G. Jung, ed.), pp. 465-509. VCH, Weinheim (1996), and Hudson (1999) *J Comb. Chem.* 1:330-360.

In one aspect, a functionalized solid phase comprises a reactive group for stably associating with a cleavable linker such as a linker shown in FIG. 2.

Figure 5A:
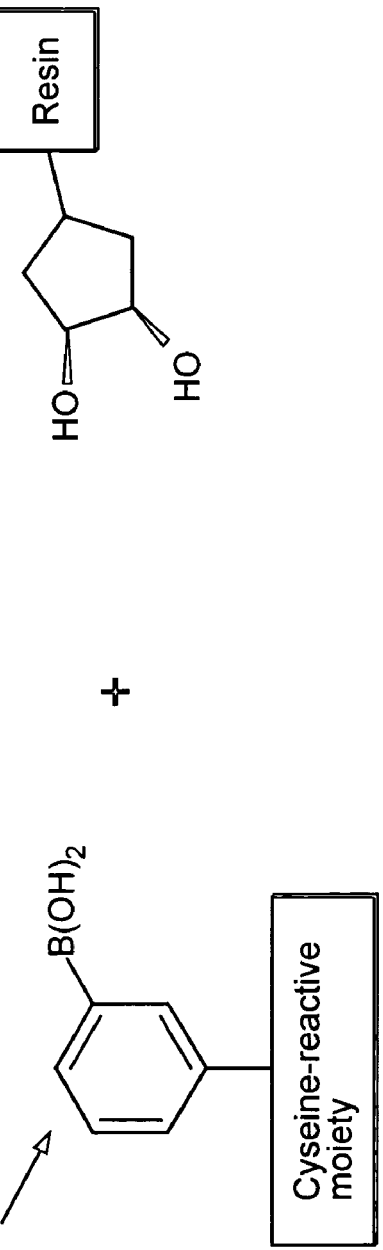
FIGS. 5A and B show two strategies for capturing and labeling cysteine-containing peptides.

In another aspect, a functionalized solid phase comprises cis hydroxy groups preferably attached by, a cyclic ring to the sold phase, or another chemical group suitable for forming a stable covalent association with an alkyl or aryl boronic acid, such as phenyl-B(OH)$_2$. In one aspect, the solid phase comprises a cyclic alkane, such as 1,2-dihydroxycyclohexane. Preferably, the cyclic alkane comprises a 5-membered ring (see, e.g., FIG. 5A).

Figure 5B:
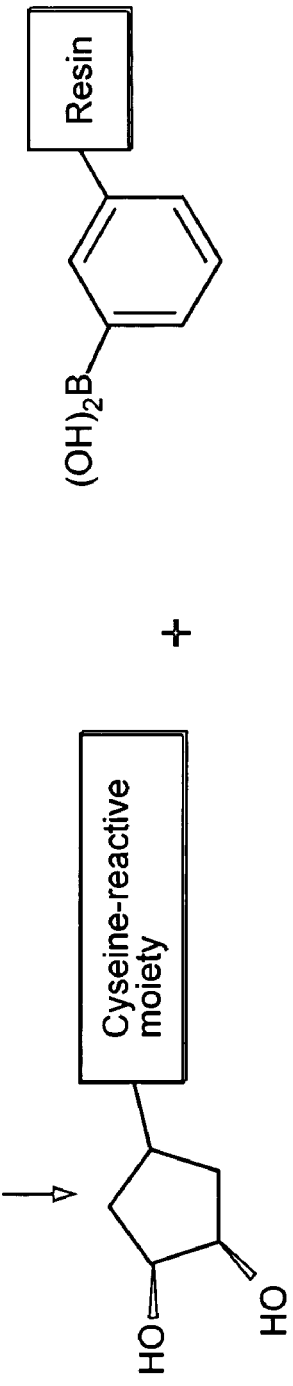
FIG. 5B shows the use of the 5-membered cyclic ring as the tag molecule and the use of R—B(OH$_2$) as the molecule which presents cis hydroxy groups to capture the tag molecule.

In a further aspect, shown in FIG. 5B, the cyclic alkane is used as a molecular tag while R—B(OH)$_2$ molecules are used to capture the tag molecules.

In another particularly useful alternative, a solid phase material is functionalized by attaching avidin molecules, which readily, reversibly complex with biotin ICAT reagents of the invention.

Methods of Using Non-Affinity Based Isotope Tags

Isolated tagged peptides according to the invention can be used to facilitate quantitative determination by mass spectrometry of the relative amounts of proteins in different samples. Also, the use of differentially isotopically-labeled reagents as internal standards facilitates quantitative determination of the absolute amounts of one or more proteins present in the sample. Samples that can be analyzed by method of the invention include, but are not limited to, cell homogenates; cell fractions; biological fluids, including, but not limited to urine, blood, and cerebrospinal fluid; tissue homogenates; tears; feces; saliva; lavage fluids such as lung or peritoneal lavages; and generally, any mixture of biomolecules, e.g., such as mixtures including proteins and one or more of lipids, carbohydrates, and nucleic acids such as obtained partial or complete fractionation of cell or tissue homogenates.

Preferably, a proteome is analyzed. By a proteome is intended at least about 20% of total protein coming from a biological sample source, usually at least about 40%, more usually at least about 75%, and generally 90% or more, up to and including all of the protein obtainable from the source. Thus the proteome may be present in an intact cell, a lysate, a microsomal fraction, an organelle, a partially extracted lysate, biological fluid, and the like. The proteome will be a mixture of proteins, generally having at least about 20 different proteins, usually at least about 50 different proteins and in most cases, about 100 different proteins or more.

Generally, the sample will have at least about 0.05 mg of protein, usually at least about 1 mg of protein or 10 mg of protein or more, typically at a concentration in the range of about 0.1-10 mg/ml. The sample may be adjusted to the appropriate buffer concentration and pH, if desired.

Using Cleavable Linkers

FIG. 1 demonstrates one proposed strategy for quantitating proteins in a sample. Suitable samples, include but are not limited to cell lysates, purified or partially purified proteins. However, the invention is particularly advantageous in that it allows protein quantification to be performed directly from cell lysates, thus minimizing the number of sample processing steps required and maximizing throughput, an essential feature of proteome analysis.

In the scheme shown in the Figure, proteins from cells are contacted with an agent (e.g., an alkylating agent) to activate one or more reactive groups on the protein so as to render these one or more groups reactive with RS groups on the tag molecule. In one aspect, the tag molecule is stably associated with a solid phase prior to reacting with cellular proteins, or can be reacted with cellular proteins first and then stably associated the solid phase. In one aspect, the tag molecule comprises a linker molecule and is bound via the linker molecule to the solid phase. Alternatively, the solid phase comprises the linker molecule and that tag molecule is contacted with the solid phase immobilized linker molecule before or after contacting the tag molecule with the solid phase and linkers. It should be obvious to those of skill in the art that the exact sequence of events can vary and that such variations are encompassed within the scope of the invention.

As shown in FIG. 1, the net result is the formation of a solid phase-linker-tag-protein complex. In the example shown in the Figure, the solid phase is a resin particle (R) and the linker comprises a cleavage site.

The complex is exposed to a protease, generating solid phase-linker-tag-peptide complexes along with untagged peptides. Suitable proteases include, but are not limited to one or more of: serine proteases (e.g., such as trypsin, hepsin, SCCE, TADG12, TADG14); metallo proteases (e.g., such as PUMP-1); chymotrypsin; cathepsin; pepsin; elastase; pronase; Arg-C; Asp-N; Glu-C; Lys-C; carboxypeptidases A, B, and/or C; dispase; thermolysin; cysteine proteases such as gingipains, and the like. Generally, the type of protease is not limiting; however, preferably, the protease is an extracellular protease. In cases in which the steps prior to protease digestion were performed in the presence of high concentrations of denaturing solubilizing agents, the sample mixture is diluted until the denaturant concentration is compatible with the activity of the proteases used.

Untagged peptides and other sample components are washed away. The remaining solid phase-linker-tag-peptide complexes are exposed to a cleavage stimulus (e.g., a chemical agent, reducing agent, light, heat, an enzyme, etc.) and the solid phase-linker portion of the complex is separated from the tag-peptide portion of the complex. Tagged peptides are subsequently analyzed by an appropriate method such as LC-MS/MS, discussed further below.

Preferably, stable isotopes are incorporated into tag molecules prior to contacting the tag with sample proteins.

In one particularly preferred aspect, proteins are obtained from cells in two different states (e.g., cells which are cancerous and non-cancerous, cells at two different developmental stages, cells exposed to a condition and cells unexposed to the condition, etc) and are activated (e.g., alkylated) for reaction with the RS groups of tag molecules. Following activation, the two cell samples are incubated with tag molecules labeled with stable isotopes, linker molecules, and solid phases (in any sequence as described above) under suitable conditions to allow solid phase-linker-tag-protein complexes to form. Preferably, tags in the two sample tubes are labeled with different labels (e.g., heavy and light isotopes).

The samples are combined in the same tube and then proteolyzed (e.g., trypsinized) and peptides which are not immobilized on the solid phase are removed by washing. Peptides are cleaved from the resin by virtue of the cleavable linker (e.g., using 50 mM DTT for a disulfide-based linker) and stable isotopes are retained with the peptides. These provide the means for quantification in a mass spectrometer members of a peptide pair differ in mass by the exact amount of mass contributed by the stable isotope. Identical peptide pairs comprise members with heavy and light isotopes or comprise a labeled member and unlabeled member. Peptide sequencing of either member of the pair can be performed by tandem mass spectrometry to identify the parent protein from which the peptide was obtained. This can be repeated on a global scale utilizing only seconds to measure and sequence each peptide. By determining ratios of labeled and unlabeled or differentially labeled peptides, the parent protein can be quantitated in each sample. Thus, protein expression profiles can be obtained for whole cell lysates which include information identifying and quantitating each protein member in the sample.

Use of pH Sensitive Anchoring Sites on Tag Molecules

A scheme for using tag molecules comprising pH sensitive anchoring sites is shown in FIG. 2. In one aspect, proteins are activated for reaction with RS groups of the tag molecule. Where the RS-group is a cysteine reactive moiety, disulfide bonds of proteins in a sample are reduced to free SH groups using a reducing agent (e.g., such as tri-n-butylphosphine, mercaptoethylamine, dithiothreitol, and the like). If required, this reaction can be performed in the presence of solubilizing agents including high concentrations of urea and detergents to maintain protein solubility.

The proteins are contacted with suitable tag molecules, such as for example a biotin ICAT reagent or a RS—R—B(OH$_2$) molecule, under conditions suitable for forming stable associations between the RS group and the activated proteins of the sample. Tag-protein complexes are reacted with one or more proteases (e.g., such as trypsin) to generate tag-peptide complexes and untagged peptides. Tagged peptides are contacted with a solid phase under conditions suitable for forming stable associations with the solid phase and untagged peptides are washed away. As above, the order of contacting with the solid phase can be varied. For example, tag molecules can be bound to the solid phase prior to contacting with proteins in a sample. Preferably, the pH is about 8.5 or higher, to maintain covalent bonding between the tag molecule and the solid phase during the contacting steps and wash steps. Reactions generally can be performed at room temperature.

The pH of the sample is reduced to less than about 8.5, and preferably to less than a pH of 3, to remove the tagged peptide from the support. As above, tagged peptides may subsequently be analyzed by LC-MS/MS. Also, as above, parallel samples contacted with differentially labeled tags can be combined for protease digestion steps, purification of tagged molecules, and subsequent analysis by LC-MS/MS to determine ratios of labeled tagged peptides in the combined sample. Optimal conditions (e.g., pH and temperature) for removing tag molecules may be determined using an assay such as described in Example 1.

Quantitation of Proteins in Samples

Whether using either the cleavable linker scheme or the pH sensitive anchoring site scheme, quantitation of proteins involves the same general principals. For the comparative analysis of several samples, one sample is designated a reference to which the other samples are related to. Typically, the reference sample is labeled with the isotopically heavy reagent and the experimental samples are labeled with the isotopically light form of the reagent, although this choice of reagents is arbitrary.

After tagging, aliquots of the samples labeled with the isotopically different reagents (e.g., heavy and light reagents, or labeled and unlabeled reagents) are combined and all the subsequent steps are performed on the pooled samples. Combination of the differentially labeled samples at this early stage of the procedure eliminates variability due to subsequent reactions and manipulations. Preferably equal amounts of each sample are combined.

Following protease digestion and purification of tagged peptides in a combined sample, the mixture of proteins is submitted to a separation process, which preferably, allows the separation of the protein mixture into discrete fractions. Each fraction is preferably substantially enriched in only one labeled protein of the protein mixture. The methods of the present invention are utilized in order to identify and/or quantify and/or determine the sequence of a tagged peptide. Within preferred embodiments of the invention, the tagged peptide is "substantially pure," after the separation procedure which means that the polypeptide is about 80% homogeneous, and preferably about 99% or greater homogeneous. Many methods well known to those of ordinary skill in the art may be utilized to purify tagged peptides. Representative examples include HPLC, Reverse Phase-High Pressure Liquid Chromatography (RP-HPLC), gel electrophoresis, chromatography, or any of a number of peptide purification methods as are known in the art.

A preferred purification method is microcapillary liquid chromatograph.

Analysis of isolated, tagged peptides by microcapillary LC-MS$^n$ or CE-MS$^n$ with data dependent fragmentation is performed using methods and instrument control protocols well-known in the art and described, for example, in Ducret et al., 1998; Figeys and Aebersold, 1998; Figeys et al., 1996; or Haynes et al., 1998. Also encompassed within the scope of the invention, although less preferred, are mass spectrometry methods such as fast atomic bombardment (FAB), plasma desorption (PD), thermospray (TS), and matrix assisted laser desorption (MALDI) methods.

In the analysis step, both the quantity and sequence identity of the proteins from which the tagged peptides originated can be determined by automated multistage MS (MS$^n$). This is achieved by the operation of the mass spectrometer in a dual mode in which it alternates in successive scans between measuring the relative quantities of peptides eluting from the capillary column and recording the sequence information of selected peptides. Peptides are quantified by measuring in the MS mode the relative signal intensities for pairs of peptide ions of identical sequence that are tagged with the molecules comprising light or heavy forms of isotope, respectively, or labeled and unlabeled members of a peptide pair, and which therefore differ in mass by the mass differential encoded within the labeled tagged reagent.

Peptide sequence information is automatically generated by selecting peptide ions of a particular mass-to-charge (m/z) ratio for collision-induced dissociation (CID) in the mass spectrometer operating in the MS$^n$ mode. (Link, A. J. et al., 1997; Gygi, S. P., et al. 1999; and Gygi, S. P. et al., 1999). The resulting CID spectra are then automatically correlated with sequence databases to identify the protein from which the sequenced peptide originated. Combination of the results generated by MS and MS$^n$ analyses of labeled tagged peptide samples therefore determines the relative quantities, as well as the sequence identities, of the components of protein mixtures in a single, automated operation.

The approach employed herein for quantitative proteome analysis is based on two principles. First, a short sequence of contiguous amino acids from a protein (5-25 residues) contains sufficient information to uniquely identify that protein. Protein identification by MS$^n$ is accomplished by correlating the sequence information contained in the CID mass spectrum with sequence databases, using computer searching algorithms known in the art (Eng, J. et al., 1994; Mann, M. et al., 1994; Qin, J. et al., 1997; Clauser, K. R. et al., 1995). Pairs of identical peptides tagged with the light and heavy affinity tagged reagents, or labeled and unlabeled peptides, respectively, (or in analysis of more than two samples, sets of identical tagged peptides in which each set member is differentially isotopically labeled) are chemically identical and therefore serve as mutual internal standards for accurate quantitation.

The MS measurement readily differentiates between peptides originating from different samples, representing for example different cell states, because of the difference between isotopically distinct reagents attached to the peptides. The ratios between the intensities of the differing weight components of these pairs or sets of peaks provide an accurate measure of the relative abundance of the peptides (and hence the proteins) in the original cell pools because the MS intensity response to a given peptide is independent of the isotopic composition of the reagents (De Leenheer, A. P. et al (1992).

Several beneficial features of the method are apparent. At least two peptides can be detected from each protein in a pooled sample mixture. Therefore, both quantitation and protein identification can be redundant. Further, where the peptide group which reacts with the RS group of a tag molecule is relatively rare (e.g., such as a cysteinyl residue), the presence of such a group in a tagged peptide adds an additional powerful constraint for database searching (Sechi, S. et al., 1998). The use of relatively rare peptide groups and the tagging and selective enrichment for peptides containing these groups significantly reduces the complexity of the peptide mixture generated by the concurrent digestion of multiple proteins and facilitates MS$^n$ analysis. For example, a theoretical tryptic digest of the entire yeast proteome (6113 proteins) produces 344,855 peptides, but only 30,619 of these peptides contain a cysteinyl residue. Additionally, the chemistries used in both schemes discussed above are compatible with LC-MS/MS analysis.

The methods described above, generally start with about 100 μg of protein and require no fractionation techniques. However, the methods are compatible with any biochemical, immunological or cell biological fractionation methods that reduce sample complexity and enrich for proteins of low abundance while quantitation is maintained. This method can be redundant in both quantitation and identification if multiple groups on a single protein bind to an RS group of a tag molecule.

The methods of this invention can be applied to analysis of low abundance proteins and classes of proteins with particular physico-chemical properties including poor solubility, large or small size and extreme p/values.

An application of the chemistry and described above is the establishment of quantitative profiles of complex protein samples and ultimately total lysates of cells and tissues.

In addition, the reagents and methods of this invention may be used to determine sites of protein modifications and therefore the abundance of modified proteins in a sample. For example, in one aspect, when the RS group reacts with a modified residue on a protein, differentially isotopically labeled tagged peptides are used to determine the sites of induced protein modification. Modified peptides are identified in a protease-digested sample mixture by fragmentation in the ion source of an ESI-MS instrument and their relative abundances are determined by comparing the ion signal intensities of an experimental sample with the intensity of an included, isotopically labeled standard. Modifications included within the scope of the invention include, but are not limited to, glycosylation, methylation, acylation, phosphorylation, ubiquination, farnesylation, and ribosylation.

In one aspect, the RS group is a Boron tag of reversed polarity, that is the two hydroxyl groups of R—B(OH$_2$) are exposed in solution to bind to glycosylated peptides. In this scenario, the Boron tag is attached to the solid phase, SP, via another type of molecule such as a catechol group.

In another aspect, a cyclic alkane comprising cis hydroxy groups are used as tag molecules while an R—B(OH$_2$) molecule is attached to a support and used to capture the tag molecules (see, e.g., FIG. 5).

In still another aspect, a biotin with an alkylating group is used as a tag molecule. The tag portion is cleaved preferably through a disulfide bond from the biotin portion, which is attached to the support through an avidin complex.

Quantitative Analysis of Surface Proteins in Cells and Tissue

The cell exterior membrane and its associated proteins (cell surface proteins) participate in sensing external signals and responding to environmental cues. Changes in the abundance of cell surface proteins can reflect a specific cellular state or the ability of a cell to respond to its changing environment. Thus, the comprehensive, quantitative characterization of the protein components of the cell surface can identify marker proteins or constellations of marker proteins characteristic for a particular cellular state, or explain the molecular basis for cellular responses to external stimuli. Indeed, changes in expression of a number of cell surface receptors such as Her2/neu, erbB, IGFI receptor, and EGF receptor have been implicated in carcinogenesis and a current immunological therapeutic approach for breast cancer is based on the infusion of an antibody (Herceptin, Genentech, Palo Alto, Calif.) that specifically recognizes Her2/neu receptor.

Cell surface proteins are also experimentally accessible. Diagnostic assays for cell classification and preparative isolation of specific cells by methods such as cell sorting or panning are based on cell surface proteins. Thus, differential analysis of cell surface proteins between normal and diseased (e.g., cancer) cells can identify important diagnostic or therapeutic targets. While the importance of cell surface proteins for diagnosis and therapy of cancer has been recognized, membrane proteins have been difficult to analyze. Due to their generally poor solubility they tend to be under-represented in standard 2D gel electrophoresis patterns and attempts to adapt 2D electrophoresis conditions to the separation of membrane proteins have met limited success. The method of this invention can overcome the limitations inherent in the traditional techniques.

Methods can be applied to enhance the selectivity for tagged peptides derived from cell surface proteins. For example, tagged cell surface proteins can be protease-digested directly on the intact cells to generate tagged peptides, purified and analyzed as discussed above. In addition, traditional cell membrane preparations may be used as an initial step to enrich cell surface proteins. These methods can include gentle cell lysis with a dounce homogenizer and series of density gradient centrifugations to isolate membrane proteins prior to proteolysis. This method can provide highly enriched preparations of cell surface proteins. In the application of the methods of this invention to cell surface proteins, once the tagged proteins are fragmented, the tagged peptides behave no differently from the peptides generated from more soluble samples.

Methods according to the invention can be used for qualitative and/or quantitative analysis of global protein expression profiles in cells and tissues, i.e., analysis of proteomes. The method can also be employed to screen for and identify proteins whose expression level in cells, tissue or biological fluids is affected by a stimulus (e.g., administration of a drug or contact with a potentially toxic material), by a change in environment (e.g., nutrient level, temperature, passage of time) or by a change in condition or cell state (e.g., disease state, malignancy, site-directed mutation, gene knockouts) of the cell, tissue or organism from which the sample originated. The proteins identified in such a screen can function as markers for the changed state. For example, comparisons of protein expression profiles of normal and malignant cells can result in the identification of proteins whose presence or absence is characteristic and diagnostic of the malignancy.

The methods herein can be employed to screen for changes in the expression or state of enzymatic activity of specific proteins. These changes may be induced by a variety of compounds or chemicals, including pharmaceutical agonists or antagonists, or potentially harmful or toxic materials. The knowledge of such changes may be useful for diagnosing abnormal physiological responses and for investigating complex regulatory networks in cells.

Compounds which can be evaluated include, but are not limited to: drugs; toxins; proteins; polypeptides; peptides; amino acids; antigens; cells, cell nuclei, organelles, portions of cell membranes; viruses; receptors; modulators of receptors (e.g., agonists, antagonists, and the like); enzymes; enzyme modulators (e.g., such as inhibitors, cofactors, and the like); enzyme substrates; hormones; nucleic acids (e.g., such as oligonucleotides; polynucleotides; genes, cDNAs; RNA; antisense molecules, ribozymes, aptamers), and combinations thereof. Compounds also can be obtained from synthetic libraries from drug companies and other commercially available sources known in the art (e.g., including, but not limited to, the LeadQuest® library) or can be generated through combinatorial synthesis using methods well known in the art. A compound is identified as a modulating agent if it alters the expression or site of modification of a polypeptide and/or if it alters the amount of modification by an amount that is significantly different from the amount observed in a control cell (e.g., not treated with compound) (setting p values to <0.05).

Compounds identified as modulating agents are used in methods of treatment of pathologies associated with abnormal sites/levels of the particular modification. For administration to a patient, one or more such compounds are generally formulated as a pharmaceutical composition. Preferably, a pharmaceutical composition is a sterile aqueous or non-aqueous solution, suspension or emulsion, which additionally comprises a physiologically acceptable carrier (i.e., a non-toxic material that does not interfere with the activity of the active ingredient). More preferably, the composition also is non-pyrogenic and free of viruses or other microorganisms. Any suitable carrier known to those of ordinary skill in the art may be used. Representative carriers include, but are not limited to: physiological saline solutions, gelatin, water, alcohols, natural or synthetic oils, saccharide solutions, glycols, injectable organic esters such as ethyl oleate or a combination of such materials. Optionally, a pharmaceutical composition additionally contains preservatives and/or other additives such as, for example, antimicrobial agents, anti-oxidants, chelating agents and/or inert gases, and/or other active ingredients.

Routes and frequency of administration, as well doses, will vary from patient to patient. In general, the pharmaceutical compositions is administered intravenously, intraperitoneally, intramuscularly, subcutaneously, intracavity or transdermally. Between 1 and 6 doses is administered daily. A suitable dose is an amount that is sufficient to show improvement in the symptoms of a patient afflicted with a disease associated an aberrant level of expression of a particular protein or the site or amount of modification of the protein. Such improvement may be detected by monitoring appropriate clinical or biochemical endpoints as is known in the art. In general, the amount of modulating agent present in a dose, or produced in situ by DNA present in a dose (e.g., where the modulating agent is a polypeptide or peptide encoded by the DNA), ranges from about 1 µg to about 100 mg per kg of host. Suitable dose sizes will vary with the size of the patient, but will typically range from about 10 mL to about 500 mL for 10-60 kg animal. A patient can be a mammal, such as a human, or a domestic animal.

The methods herein can also be used to implement a variety of clinical and diagnostic analyses to detect the presence, absence, deficiency or excess of a given protein or protein function in a biological fluid (e.g., blood), or in cells or tissue. The methods are particularly useful in the analysis of complex mixtures of proteins, i.e., those containing 5 or more distinct proteins or protein functions. Therefore in one aspect, the methods are used to compare and quantitate levels of proteins and/or sites and amounts of protein modifications in samples between a normal cell sample and a cell sample from a patient with a pathological condition (preferably, the cell sample is the target of the pathological condition) in order to identify the presence, absence, deficiency or excess of a given protein or protein function which is associated with the pathological condition.

Kits

The invention further provides a kit comprising reagents and/or compositions as described above. For example, in one aspect the invention provides a tag molecule and one or more of a reagent selected from the group consisting of: an activating agent for providing active groups on a protein which bind to the reactive site of the tag molecule; a solid phase; one or more agents for lysing a cell; a pH controlling agent; a reducing agent; one or more proteases; one or more cell samples or fractions thereof. In one aspect, the tag molecule is further stably associated with a peptide, i.e., a tagged reference peptide is included suitable for a particular assay of choice.

The invention also provides kits comprising a plurality of tagged peptide molecules, each tagged peptide molecule comprising a peptide and a tag molecule stably associated with the protein, the tag molecule further comprising an isotope label, and a pH and/or reduction sensitive anchoring site for anchoring the tag molecule to a solid phase. In one aspect, the kit comprises pairs of tagged peptides and each member of a pair of tagged peptides comprises an identical peptide and is differentially labeled from the other member of the pair. In another aspect, the kit comprises at least one set of tagged peptides, the set comprising different peptides corresponding to a single protein. In still another aspect, at least one set of tagged peptides comprises peptides corresponding to modified and unmodified forms of a single protein. In a further aspect, the kit comprises at least one set of tagged peptides from a first cell at a first cell state and at least one set of tagged peptides from a second cell at a second cell state. For example, the first cell may be a normally proliferating cell while the second cell is an abnormally proliferating cell (e.g., a cancer cell). First and second cells may also represent different stages of cancer, different developmental stages, cells exposed to agents (e.g., drugs, potentially toxic or carcinogenic materials) or conditions (e.g., pH, temperature, nutrient levels, passage of times) and cells not exposed to agents or conditions, as well as cells which do or do not express particular recombinant DNA constructs.

EXAMPLES

The invention will now be further illustrated with reference to the following examples. It will be appreciated that what follows is by way of example only and that modifications to detail may be made while still falling within the scope of the invention.

Example 1

Arylboronic Acids as New ICAT Reagents

Arylboronic Acid-Immobilized Glutathione on a Carbohydrate Affinity Column

A column of carbohydrate was immobilized on agarose (Calbiochem, gal-α-1,3-gal on agarose, cat. # 215364, 2 mls packed resin) using 0.05% SDS in 50 mM ammonium bicarbonate, pH=8.1; however, SDS may be omitted. The column was equilibrated with at least 10 column volumes of the 50 mM AmBic, without detergent, before sample was applied. An arylboronic conjugate was synthesized using standard chemistries. 68 mgs GSH in 1.9 mls of water was combined with 100 μL of 1M potassium phosphate, pH=7.4 and stirred for 5 minutes. 8.8 mgs of arylboronic acid were added which dissolved within about 15 minutes.

The scheme for generating the conjugates is shown below:

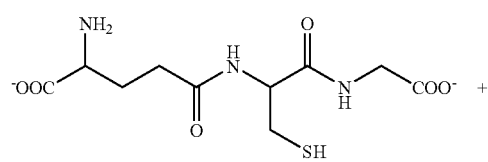

Glutathione (GSH), M.W. = 307.33
71 mgs
230.5 μmol

MPBA, M.W. = 216.99
10 mgs
46.1 μmol

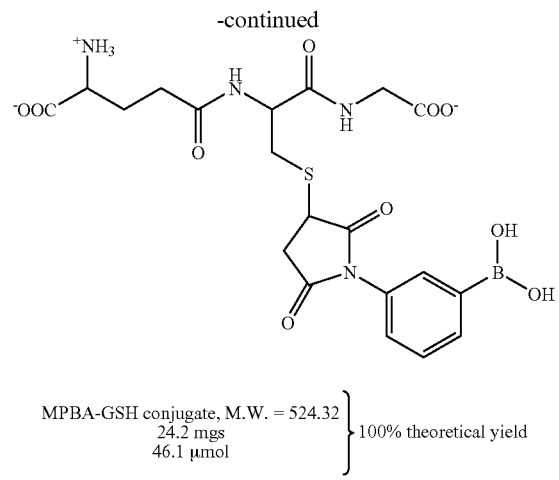

MPBA-GSH conjugate, M.W. = 524.32
24.2 mgs } 100% theoretical yield
46.1 μmol

Figure 4:
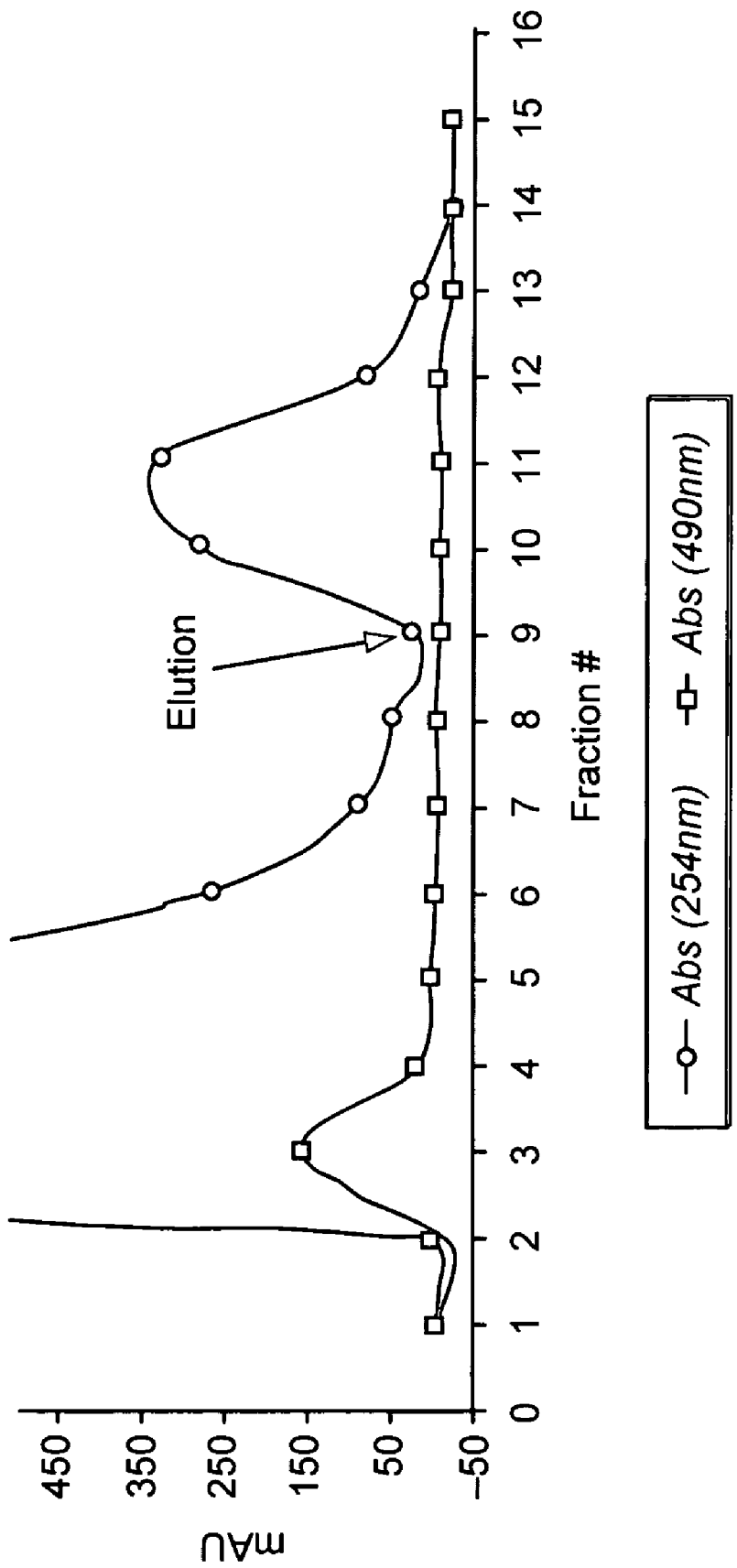
FIG. 4 shows the elution profile for a carbohydrate affinity column demonstrating pH sensitive attachment of boron-based tag molecules.

One ml of AmBic (1M) was added and the solution was stirred another 5 minutes, after which 100 μL of 150 μM fluoresceine was added. The column was washed with 50 mM AmBic solution at a flow rate of about 1 ml/minute. Five ml fractions were collected and the amount of fluorescein in the fractions was determined. A large amount of fluoresceine initially eluted. After collecting fraction 9, elution buffer consisting of 100 mM glycine, pH=2.5, and containing 25 mM glucose was used to wash the column. Five ml fractions were collected through column 15. Absorbance was determined at 254 and 490 nm, to determine the presence of aryl groups and fluoresceine respectively, in the fractions. The elution profile is shown in FIG. 4.

Fraction 10 showed significant amount of product. Fractions 10-12 were combined and saved as a combined sample (combined sample 1) at −80° C. for LC-MS analysis, as were the flow-through fractions 3-6 (combined sample 2). Thus, even without optimal conditions for recovery, significant amounts of product were recovered.

These results demonstrate that boronic acid conjugates can be used to provide pH sensitive molecular tags which can be recovered at high efficiency.

Example 2

Biotin Derivatives as New Catch and Release Reagents

Preparation of new Biotin Derivatives

A series of new biotin based ICAT reagents are provided by the invention which comprise a biotin residue and alkylating group which are connected by a linker. Preferred alkylating groups are suitable for alkylating serine residues of polypeptides. Preferred Biotin derivatives comprise biotin and a 2-[2-(2-iodo-acetylamino)-1,1-dimethyl-ethyldisulfanyl]-3-methyl-butyric acid coupled through a di(2-aminoethyl)ether, which may have one or more ethylene glycol repeat units interposed between the amino residues, e.g., a linker of the formula: —NH((CH$_2$)$_2$O)$_n$ (CH$_2$)$_2$NH—, where n is an integer of from 0 to about 5.

Figure 6B:
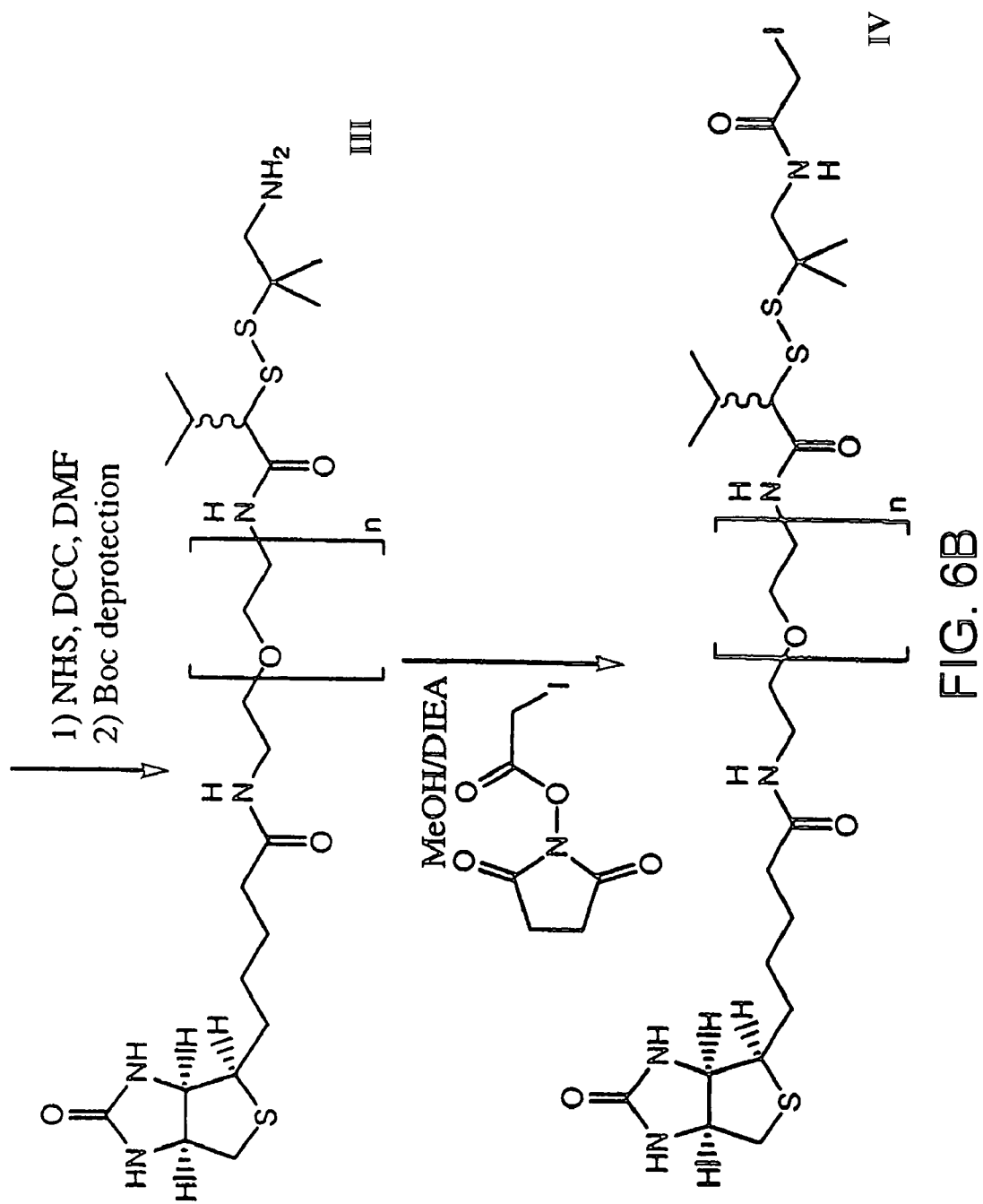
FIG. 6 is a synthetic protocol for preparing biotin based chemistries to tag peptides according to one aspect of the invention.

Biotin derivatives can be prepared by coupling of biotin, linker group and alkylating group in sequential amide bond forming reactions and amine deprotection steps. An illustrative synthesis is provided in the scheme of FIG. 6 (Boc is C(O)O'Bu, NHS is N-hydroxy succinimide, DCC is dicyclohexylcarbodiimide, DMF is N,N-dimethylformamide, and DIEA is diisopropylethylamine, and n is an integer from 0 to about 5).

Examples of biotin derivatives prepared in this manner include:

ml/min, detection at 214 nm. Mobile phase A was 5% acetonitrile (ACN) in $H_2O$, 0.06% trifluoroacetic acid (TFA), and mobile phase B was 95% ACN in $H_2O$, 0.06% TFA. Mobile phase composition was varied over elution time as follows: $t_{0min}$, 5% B; $t_{5min}$, 5% B; $t_{20min}$, 50% B, $t_{25min}$, 50% B; $t_{26min}$, 100% B (4 mls/min); $t_{28min}$, 100% B (4 mls/min); $t_{30min}$, 5% B (3 mls/min).

Figure 7:
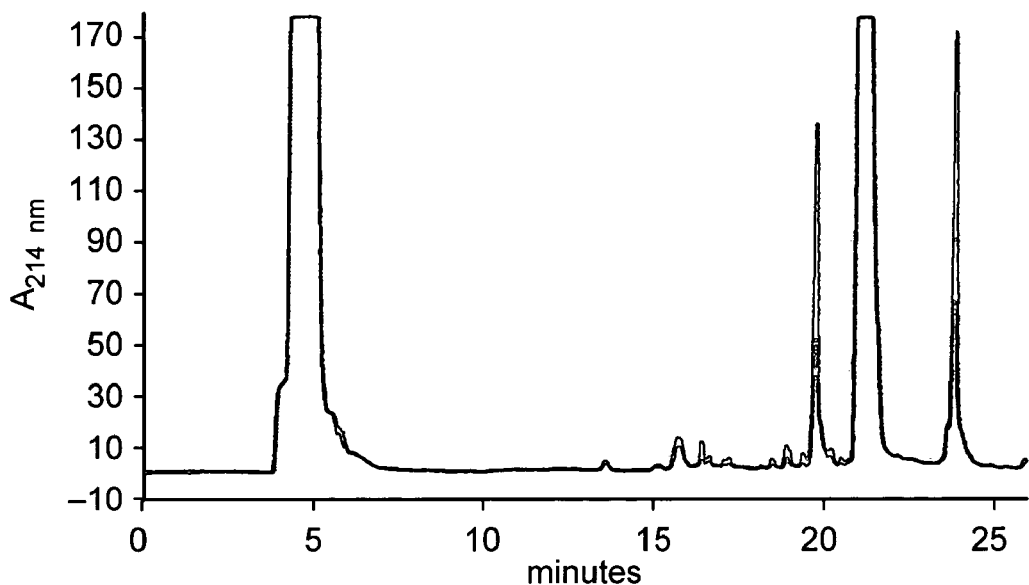
FIG. 7 is an HPLC trace of the reaction mixture in the preparation of biotin derivative IV.

FIG. 7 is an HPLC trace of the crude reaction mixture. The off-scale peak at about 22 minutes corresponded to the product (Compound IV) and was isolated. The eluent cor-

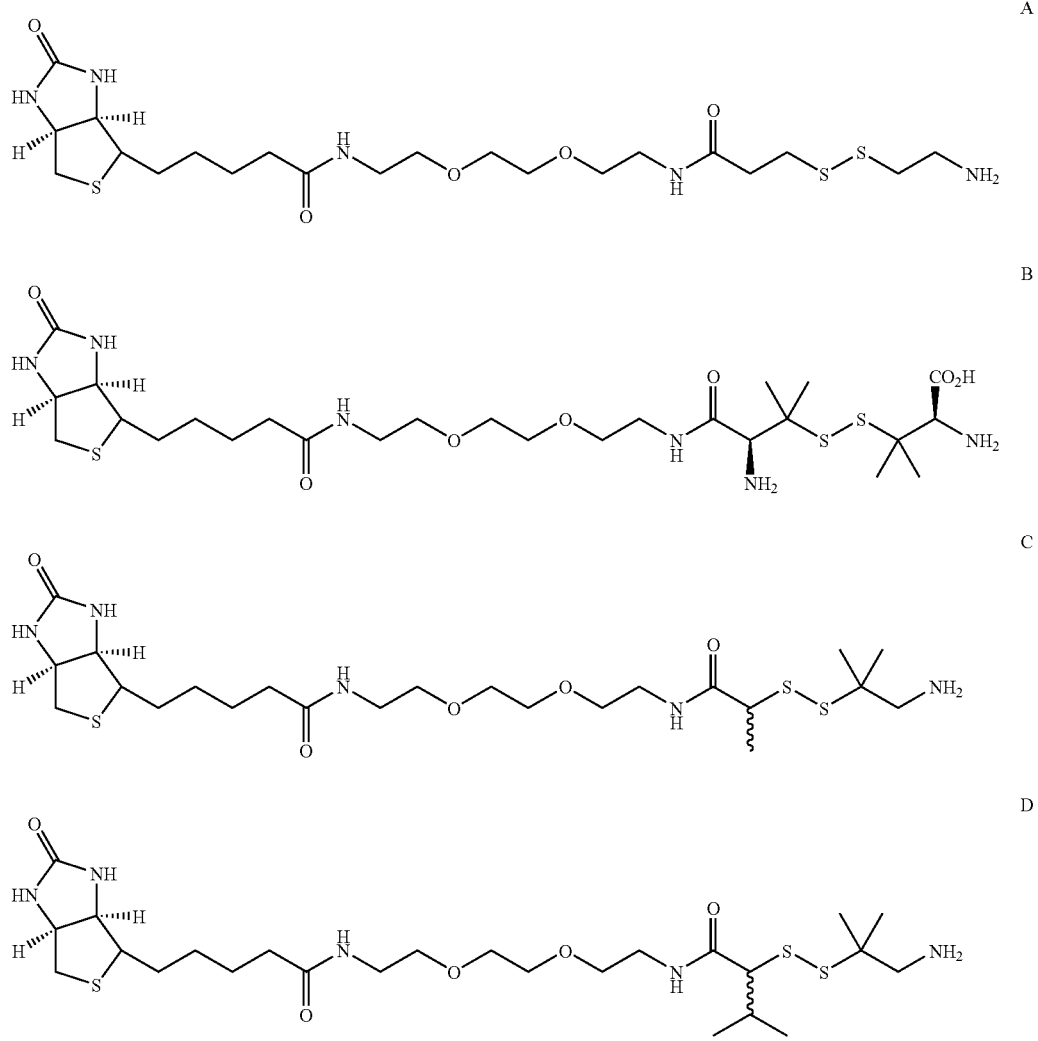

Experimental Conditions for Amide Coupling to Generate Biotin Derivative (IV)

Figure 8:
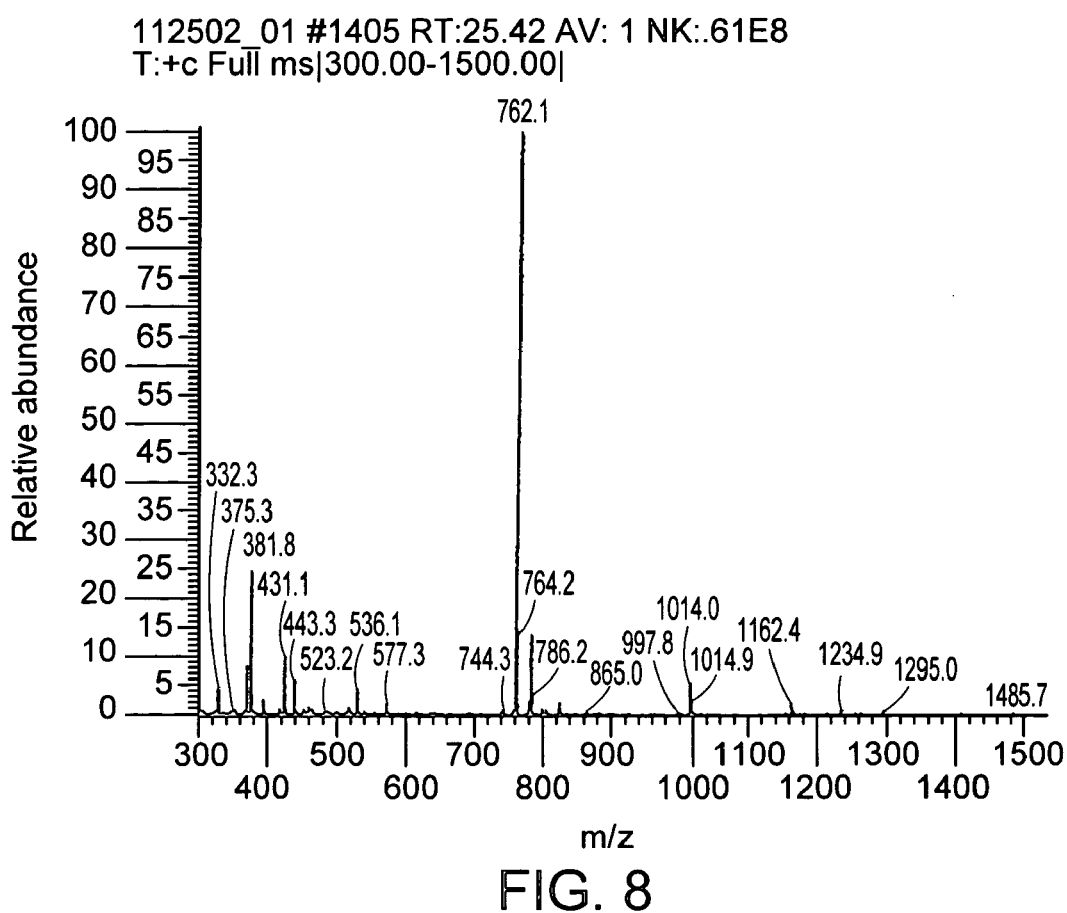
FIG. 8 is an LC-MS spectrogram of the peak corresponding to biotin derivative (IV) in the HPLC trace of FIG. 7.

Intermediate (III) (12.5 mgs) was combined with an excess of iodo-acetic acid 2,5-dioxo-pyrrolidin-1-yl ester (about 6 mgs) in methanol. One equivalent of DIEA (diluted in methanol) and additional methanol (about 0.5 mL) were added to the reaction mixture. After stirring for 30 minutes, an aliquot of reaction mixture spotted on a thin layer chromatography plate did not stain when exposed to ninhydrin solution indicating an absence of residual amino functionality. The biotin derivative (IV) was purified using reverse phase HPLC. (column was 1×25 cm, flow rate 1 responding to the 22 minute peak from several HPLC runs was combined an lyophylized in the dark without heating to afford compound (IV) as a fluffy white solid (8.3 mgs; 60% yield). FIG. 8 provides an LC-MS trace of the fluffy white powder which has a single peak at 762 which corresponded to the $[M+H]^{+1}$ peak of the biotin derivative (IV).

Example 3

Preparation of Biotin Conjugates

Conjugates of biotin derivative (IV) with glutatione may be prepared according to the scheme shown below:

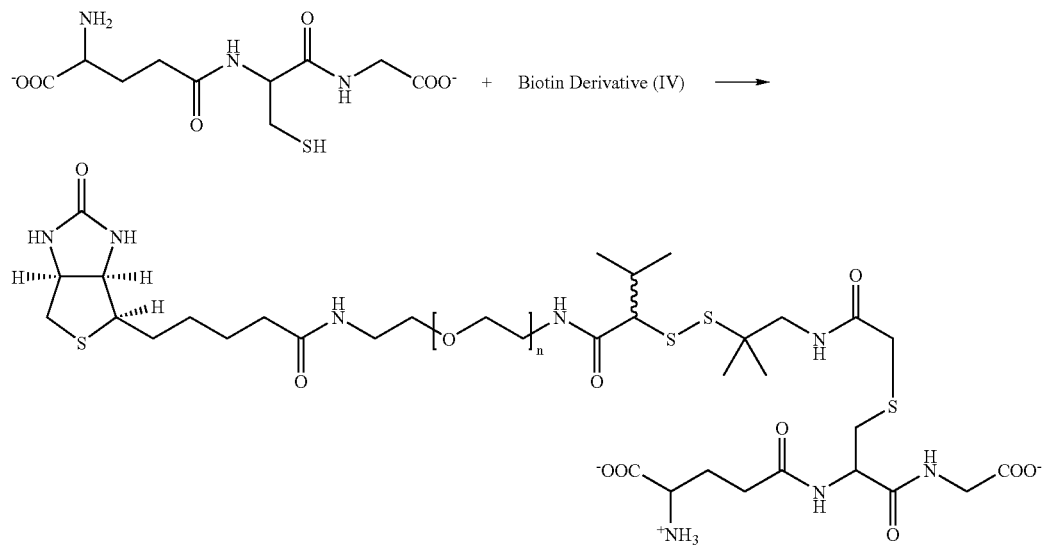

A 25 mM stock solution of the Biotin derivative (IV) in DMSO was prepared and then diluted with 50 mM Tris buffer, pH=8.0 to a final concentration of 250 µM. A 150 µM stock solution of glutatione (GSH) in 50 mM Tris buffer was also prepared. The Biotin derivative (IV) stock solution and the GSH stock solution were mixed (1:1 by volume) and incubated for thirty minutes.

A reference solution of the Biotin derivative (IV) was prepared by diluting the 25 mM DMSO solution with 50 mM Tris buffer, pH=8.0 to a final concentration of 125 µM.

Figure 9:
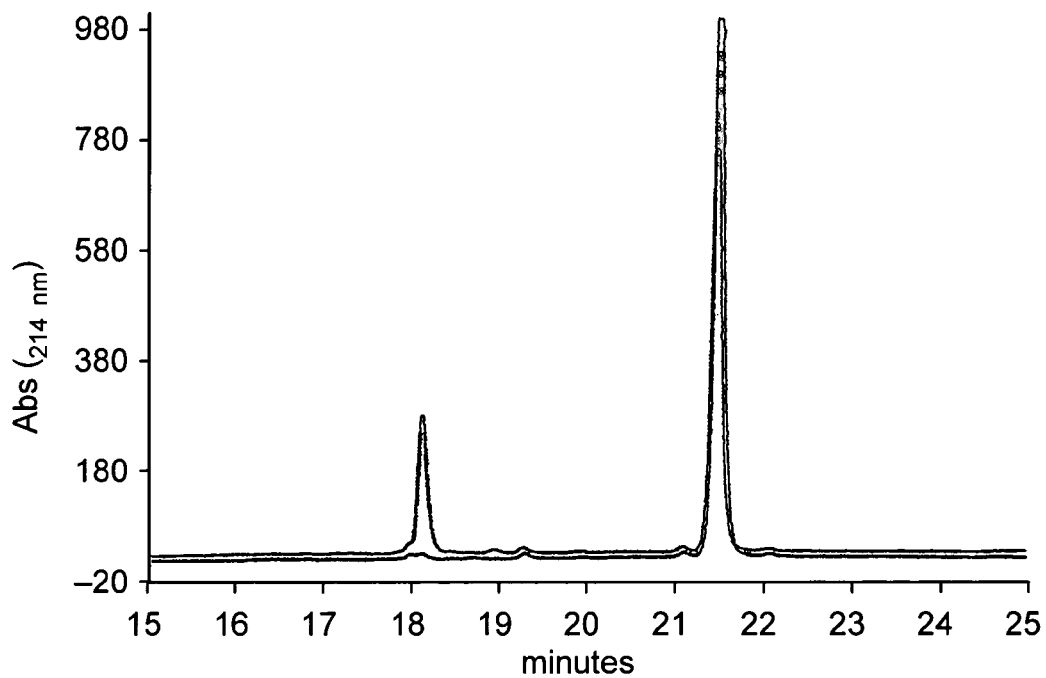
FIG. 9 is a reverse phase HPLC trace of the reaction mixture of Example 3.

FIG. 9 provides reverse phase HPLC traces of the reaction mixture and reference solution. The Reverse-phase HPLC analysis was conducted using a 2.0×250 mm column. The peak at about 21.5 minutes corresponds to unreacted biotin derivative (IV) and the product GSH conjugate eluted at about 18 minutes.

Example 4

Polypeptide-Biotin Conjugates

Figure 10:
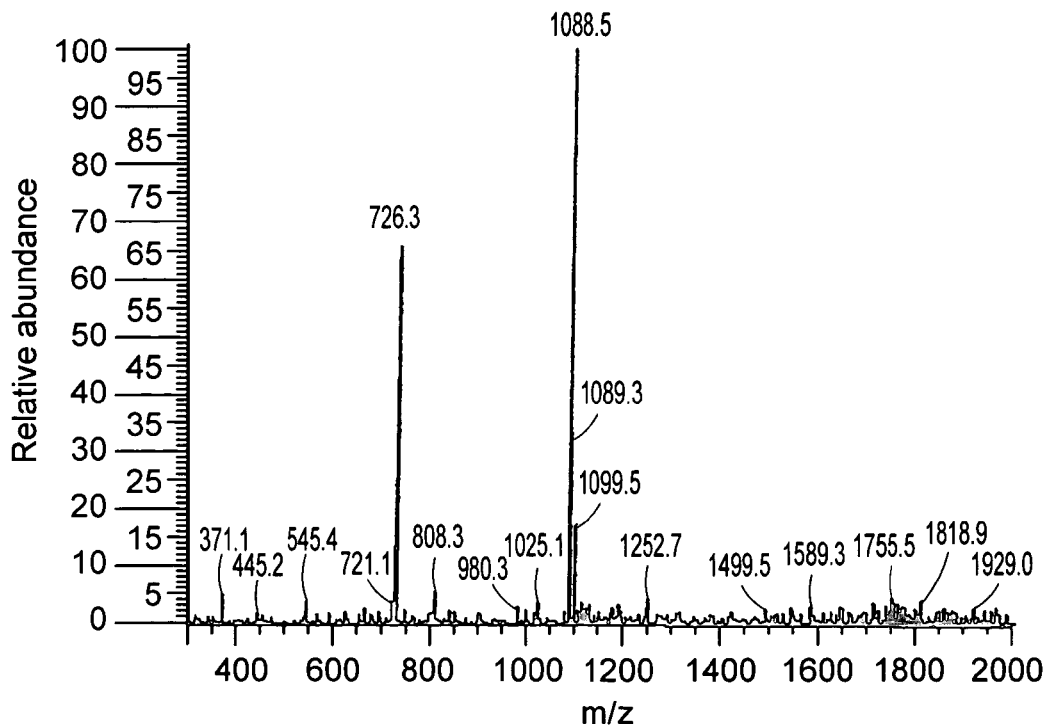
FIG. 10 is the MS spectrogram of the active site (residues 200-221) of human protein tyrosine phosphatase IB (PTP1B) having a sequence ESGSLSPEHGPVVVHCSAGIGR (SEQ ID NO: 1) where $[M+H]^{+1}=2176.4$ and $[M+2H]^{+2}=1088.7$.

A conjugate between biotin derivative IV and a peptide corresponding to the active site (residues 200-221) of human protein tyrosine phosphatase IB (PTP1B) having a sequence ESGSLSPEHGPVVVHCSAGIGR (SEQ ID NO: 1) and (MS trace shown in FIG 10: $[M+H]^{+1}$=2176.4 and $[M2H]^{+2}$=1088.7) was prepared and purified. The polypeptide was tagged at cysteine-215

Step 1. Synthesis

A 44 µL aliquot of a stock solution of PTP1B (10 nmol) was diluted with 454 µL of 100 mM ammonium carbonate (pH=8.0) containing 10% methanol. A five fold excess of Biotin derivative (IV) (2 µL of a 25 mM DMSO solution, 50 nmol) was added to the reaction mixture (final volume=500 µL). After incubating the reaction mixture for 15 minutes at room temperature, 5 µL of D-penicillamine (3,3-dimethyl-D-cysteine; D-PEN) (100 mM stock solution, 500 nmol) was introduced into the reaction mixture to consume residual Biotin derivative (IV).

Figure 11:
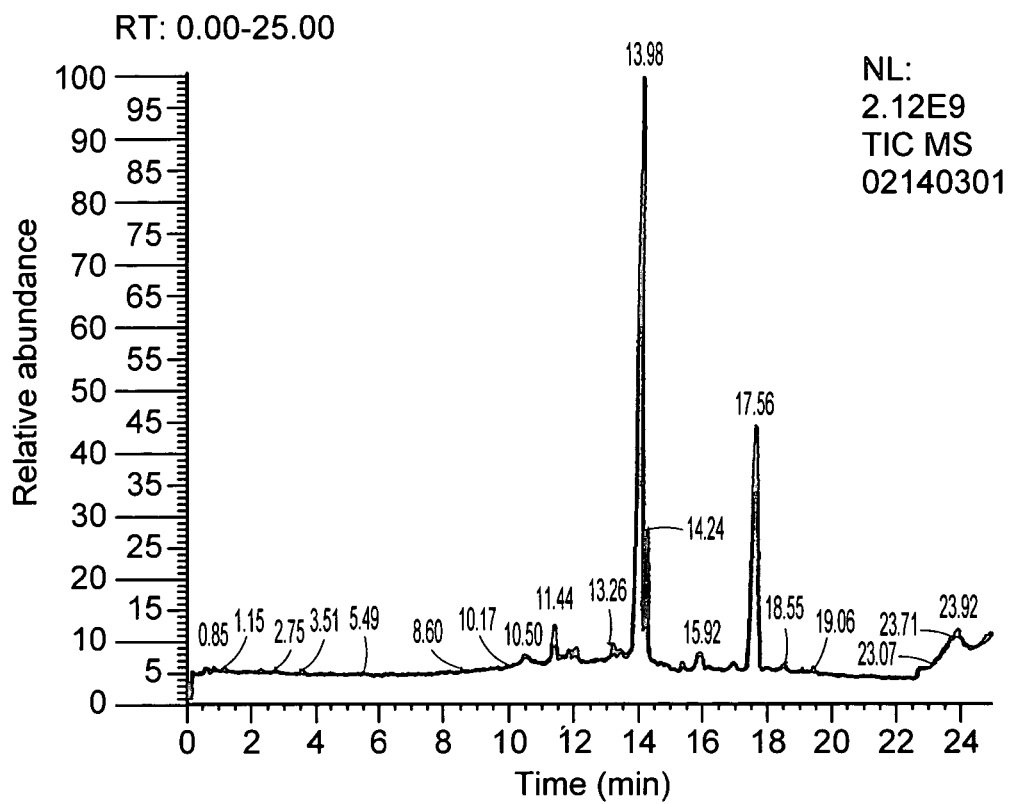
FIG. 11 is an HPLC trace of Example 4 in which the peak at 14.24 minutes corresponds to the conjugate of PTPIB.
Figure 12:
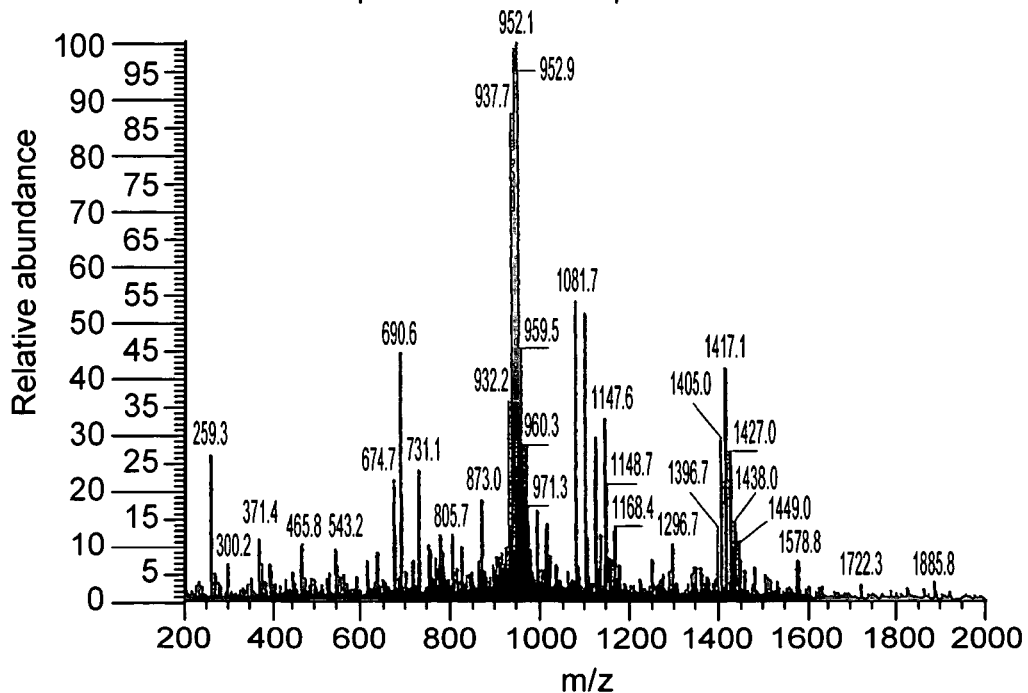
FIG. 12 is a MS spectrogram of the reaction mixture in the synthesis of the conjugate of PTP1B.

FIG. 11 is an HPLC trace of the reaction mixture had a peak at 14.24 minutes corresponding to the conjugate. The mass spectrum shown in FIG. 12 includes peaks corresponding the $[M+2H]^{+2}$ and the $[M+3H]^{+3}$ peaks at 1405.5 and 937 atomic mass units. Various sodium adducts for each peak are also present in the Mass spectrum of FIG. 12.

The HPLC trace shown in FIG. 11 also contains peaks corresponding to unreacted PTP1B (11.44 minutes) and an adduct which may result from coupling of the D-PEN and non-conjugated peptide. One skilled in the art will recognize that extended incubation times and other process optimization may be beneficial to maximize the yield of the desired conjugate and reduce by-product formation.

Figure 13:
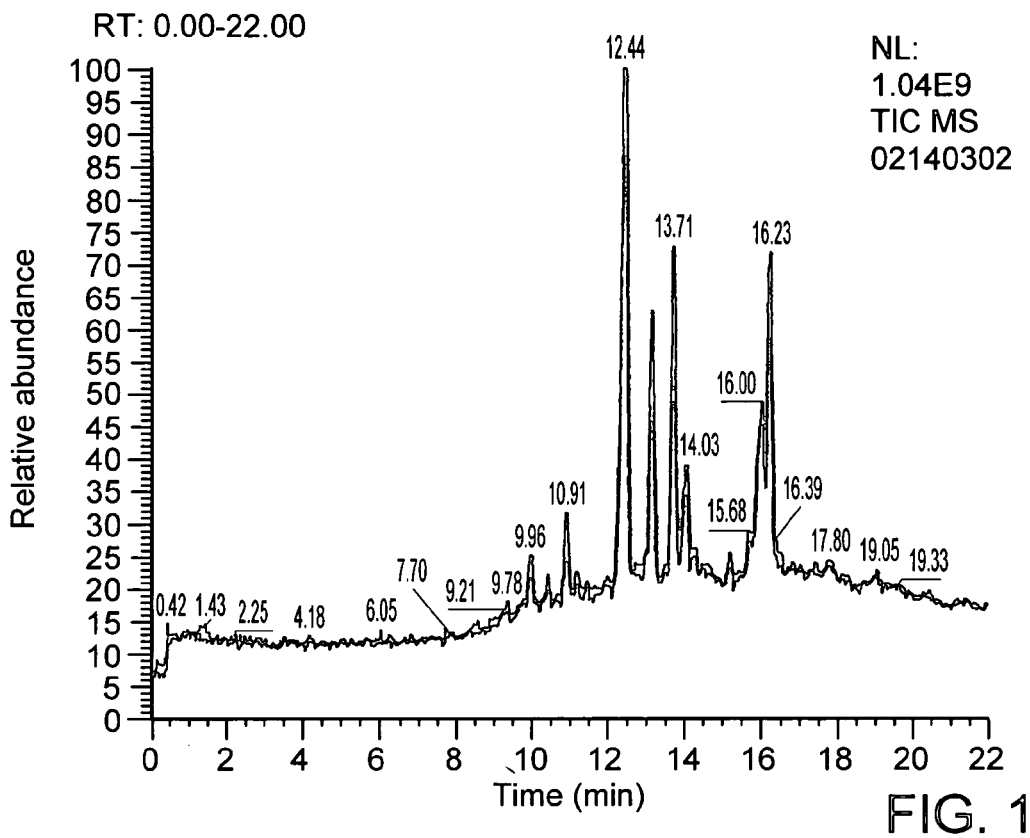
FIG. 13 a MS spectrogram of the reaction mixture in the synthesis of the conjugate of PTP1B after reduction with TCEP.

Tris(2-carboxyethyl)phosphine hydrochloride(TCEP) (5 mM final concentration) was added to the reaction mixture as a reductant. FIG. 13 is a MS chromatograph trace of the reduced reaction mixture. The solution is a mixture of PTP1B conjugate and various byproducts including a conjugate of D-PEN.

Step 2: Purification of the Conjugate

Figure 14:
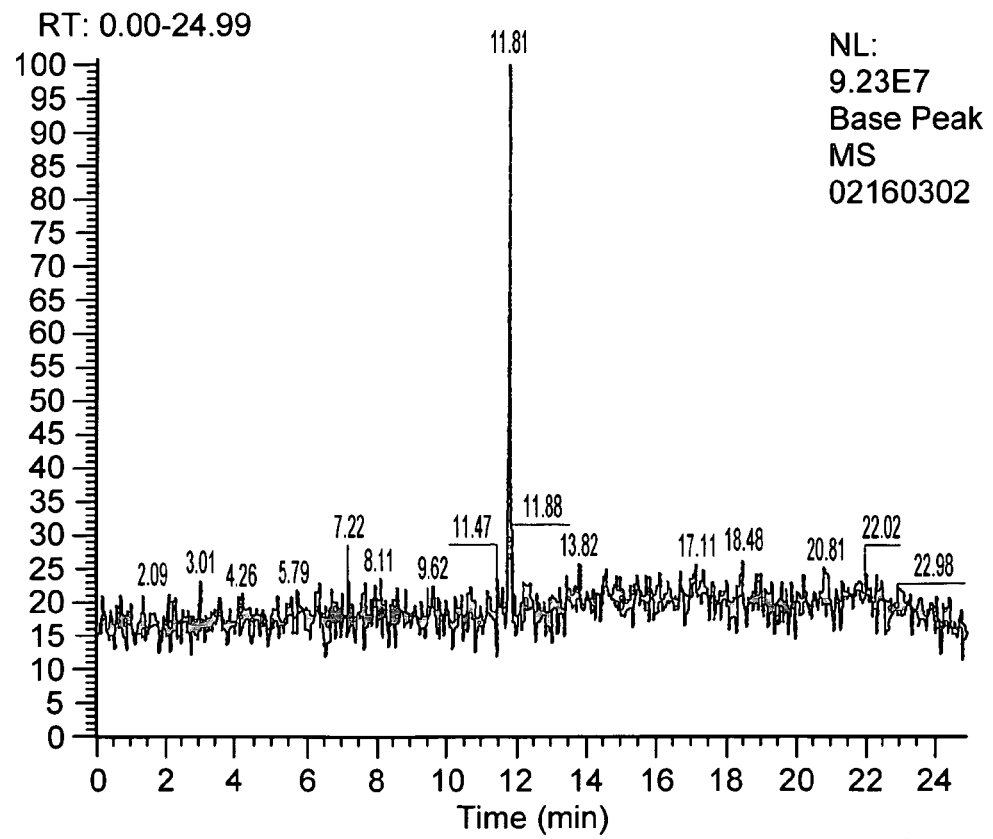
FIG. 14 is a HPLC trace of the purified conjugate of PTP1B.
Figure 15:
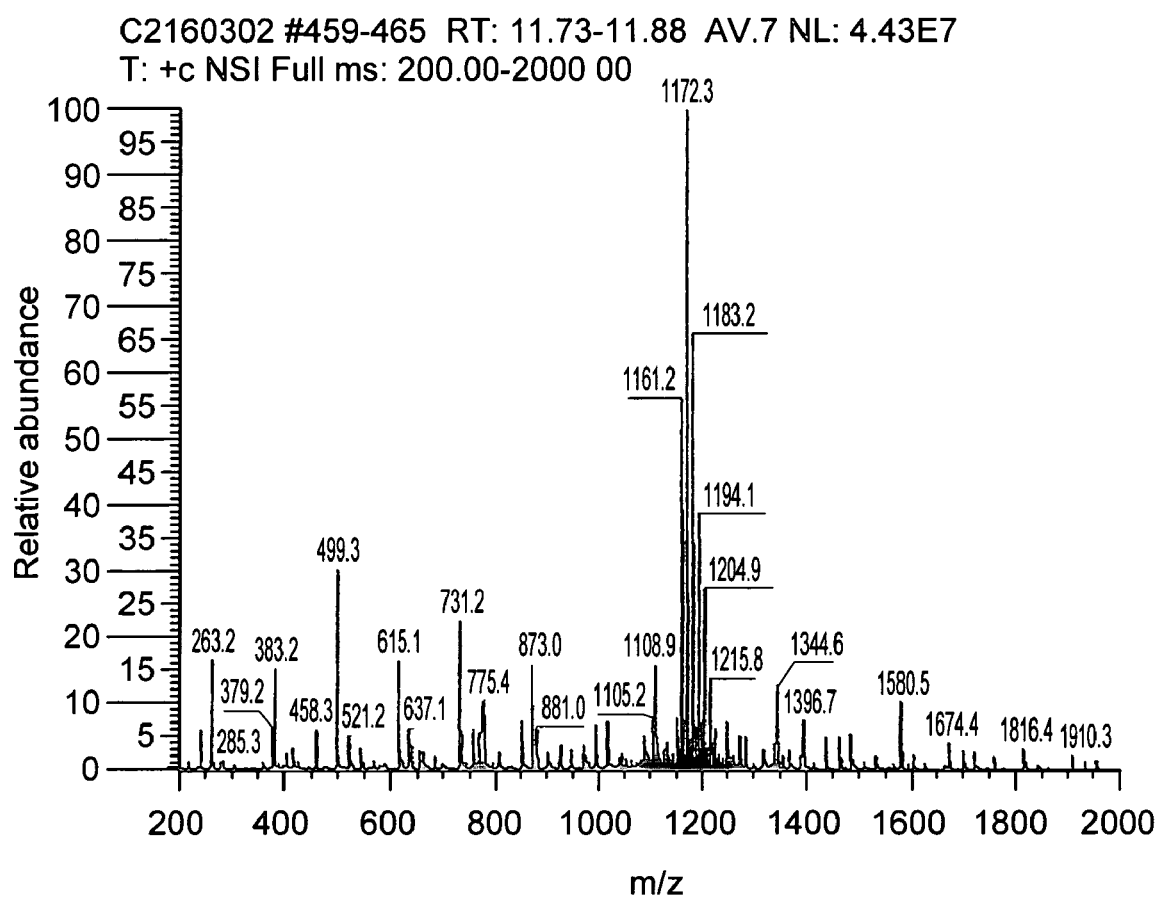
FIG. 15 is a MS spectrogram sampling the peak at 11.81 minutes in the HPLC trace of FIG. 14.

Two tubes were charged with 150 µL aliquots of the reaction mixture prepared in Step 1 (each aliquot contained the desired conjugate, about 15 nmol total biotin, and roughly 3 nmol test peptide). Packed immobilized avidin (600 µL having about 24 mmol total biotin binding capacity) was introduced into each tube and the heterogeneous mixtures were agitated for 20 minutes at room temperature. The mixtures were transferred to a spinning filter and the liquid phase removed by filtration. The beads were washed with 300 µL of an aqueous ammonium bicarbonate buffer containing 10% methanol and the supernatant removed in a centrifuge. The washing cycle was repeated twice (three total wash cycles) before the beads were resuspended in a clean ammonium bicarbonate buffer solution containing 5 mM TCEP. The solution was incubated at 40° C. for 45 minutes and then the liquid phase was collected using a spinning filter. The beads were washed and filtered twice with 100 µL aliquots of fresh ammonium bicarbonate buffer containing no additional TCEP. The TCEP containing liquid phase and subsequent washings were combined and the washings combined with the original solution to afford the conjugate in 780 µL of solution. A sample was diluted four fold with mass spec loading buffer and 2 µL of this solution analyzed by LC-MS. The LC trace of the LC-MS analysis had a single peak at 11.81 minutes and is depicted in FIG. 14. The MS spectrogram of the peak at 11.81 minutes is depicted in FIG. 15 and exhibited a a $[M+H]^{+1}$ of 1161 corresponding to the conjugate of PTP1B.

Example 5

Tagged Peptide

Figure 16A:
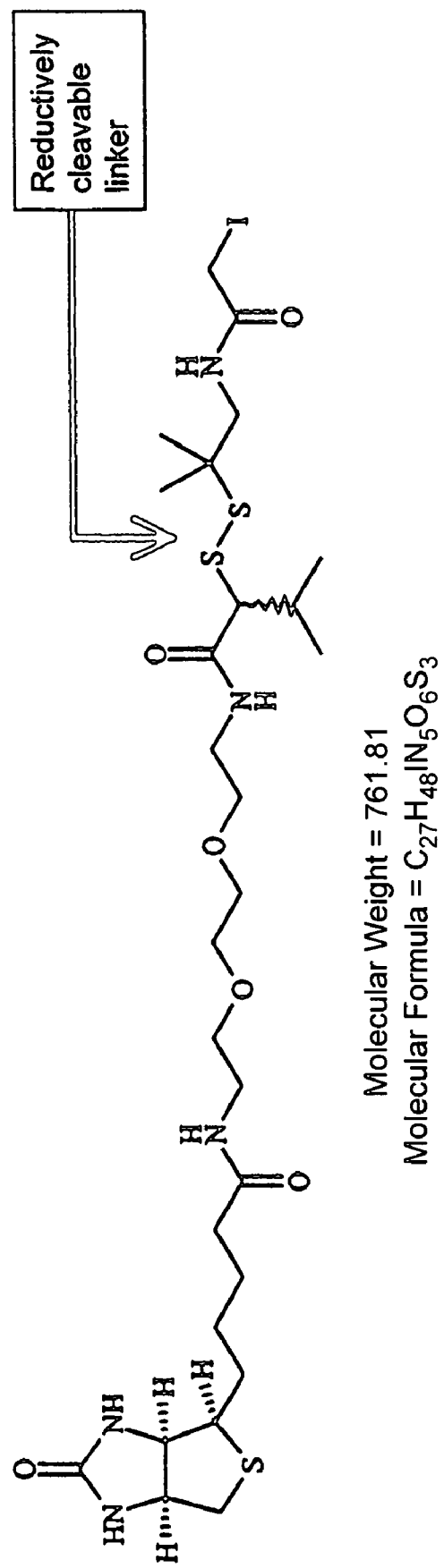
FIG. 16A illustrates the formula for a preferred catch and release (CAR) reagent for protein profiling.

A particularly useful biotin release reagent is illustrated in FIG. 16A. It can be noted that this is Biotin derivative IV where n=2. The tag is made light and also heavy with $C^{13}$ atoms for labeling the Cys residue in proteins. Fragmentation of a protein is not affected by the tag. Pairs of tagged peptides are provided by digestion and cleavage. See, e.g., the peptide ESGSLSPEHGPVVVHCSAGIGR (SEQ ID NO: 1) as illustrated in FIG. 16B.

This biotin release reagent can be treated for 30 minutes in 5 mM TCEP as described above, obtaining 95% cleavage yield.

REFERENCES

Ashikaga, K. et al. (1988) Bull. Chem. Soc. Jpn. 61:2443-2450.

Bayer, E. and Wilchek, M. (eds.) "Avidin=Biotin Technology," (1990) Methods Enzymol. 184:49-51.

Bleasby, A. J. et al. (1994), "OWL—a non-redundant composite protein sequence database," Nucl. Acids Res. 22:3574-3577.

Boucherie, H. et al. (1996), "Two-dimensional gel protein database of Saccharomyces cerevisiae," Electrophoresis 17:1683-1699.

Brockhausen, I.; Hull, E.; Hindsgaul, O.; Schachter, H.; Shah, R. N.; Michnick, S. W.;

Carver, J. P. (1989) Control of glycoprotein synthesis. J. Biol. Chem. 264,11211-11221.

Chapman, A.; Fujimoto, K.; Kornefeld, S. (1980) The primary glycosylation defect in class E Thy-1-negative mutant mouse lymphoma cells is an inability to synthesize dolichol-P-mannose. J. Biol. Chem. 255, 4441-4446.

Chen, Y.-T. and Burchell, A. (1995), The Metabolic and Molecular Bases of Inherited Disease, Scriver, C. R. et al. (eds.) McGraw-Hill, N.Y., pp. 935-966.

Clauser, K. R. et al. (1995), "Rapid mass spectrometric peptide sequencing and mass matching for characterization of human melanoma proteins isolated by two-dimensional PAGE," Proc. Natl. Acad. Sci. USA 92:5072-5076.

Cole, R. B. (1997) Electrospray Ionization Mass Spectrometry: Fundamentals, Instrumentation and Practice, Wiley, N.Y.

De Leenheer, A. P. and Thienpont, L. M. (1992), "Application of isotope dilution-mass spectrometry in clinical chemistry, pharmacokinetics, and toxicology," Mass Spectrom. Rev. 11:249-307.

DeRisi, J. L. et al. (1997), "Exploring the metabolic and genetic control of gene expression on a genomic scale," Science 278:680-6

Dongr'e, A. R., Eng, J. K., and Yates, J. R., 3rd (1997), "Emerging tandem-mass-spectrometry techniques for the rapid identification of proteins," Trends Biotechnol. 15:418-425.

Ducret, A., VanOostveen, I., Eng, J. K., Yates, J. R., and Aebersold, R. (1998), "High throughput protein characterization by automated reverse-phase chromatography/electrospray tandem mass spectrometry," Prot. Sci. 7:706-719.

Eng, J., McCormack, A., and Yates, J. I. (1994), "An approach to correlate tandem mass spectral data of peptides with amino acid sequences in a protein database," J. Am. Soc. Mass Spectrom. 5:976-989.

Figeys, D. et al. (1998), "Electrophoresis combined with mass spectrometry techniques: Powerful tools for the analysis of proteins and proteomes," Electrophoresis 19:1811-1818.

Figeys, D., and Aebersold, R. (1998), "High sensitivity analysis of proteins and peptides by capillary electrophoresis tandem mass spectrometry: Recent developments in technology and applications," Electrophoresis 19:885-892.

Figeys, D., Ducret, A., Yates, J. R., and Aebersold, R. (1996), "Protein identification by solid phase microextraction-capillary zone electrophoresis-microelectrospray-tandem mass spectrometry," Nature Biotech. 14:1579-1583.

Figeys, D., Ning, Y., and Aebersold, R. (1997), "A microfabricated device for rapid protein identification by microelectrospray ion trap mass spectrometry," Anal. Chem. 69:3153-3160.

Freeze, H. H. (1998) Disorders in protein glycosylation and potential therapy. J. Pediatrics 133, 593-600.

Freeze, H. H. (1999) Human glycosylation disorders and sugar supplement therapy. Biochem. Biophys. Res. Commun. 255, 189-193.

Gamper, H. B., "Facile preparation of nuclease resistant 3'-modified oligodeoxy-nucleotides," Nucl. Acids Res., 21:145-150 (January 1993)

Garrels, J. I., McLaughlin, C. S., Warner, J. R., Futcher, B., Latter, G. I., Kobayashi, R., Schwender, B., Volpe, T., Anderson, D. S., Mesquita, F.-R., and Payne, W. E. (1997), "Proteome studies of Saccharomyces cerevisiae: identification and characterization of abundant proteins. Electrophoresis," 18:1347-1360.

Gerber, S. A.; Scott, C. R.; Turecek, F.; Gelb, M. H. (1999) Analysis of rates of multiple enzymes in cell lysates by electrospray ionization mass spectrometry. J. Am. Chem. Soc. 121, 1102-1103.

Glaser, L. (1966) Phosphomannomutase from yeast. In Meth. Enzymol. Vol. Vil, Neufeld, E. F.; Ginsburg, V. Eds; Academic Press: N.Y. 1966, pp. 183-185.

Gygi, S. P. et al. (1999), "Correlation between portein and mRNA abundance in yeast," Mol. Cell. Biol. 19:1720-1730.

Gygi, S. P. et al. (1999), "Protein analysis by mass spectrometry and sequence database searching: tools for cancer research in the post-genomic era," Electrophoresis 20:310-319.

Haynes, P. A., Fripp, N., and Aebersold, R. (1998), "Identification of gel-separated proteins by liquid chromatography electrospray tandem mass spectrometry: Comparison of methods and their limitations," Electrophoresis 19:939-945.

Hodges, P. E. et al. (1999), "The Yeast Proteome Database (YPD): a model for the organization and presentation of genome-wide functional data," Nucl. Acids Res. 27:69-73.

Johnston, M. and Carlson, M. (1992), in The Molecular and Cellular Biology of the Yeast Saccharomyces, Johnes, E. W. et al. (eds.), Cold Spring Harbor Press, New York City, pp. 193-281.

Kataky, R. et. al. J Chem Soc Perk T 2 (2) 321-327 FEB 1990.

Kaur, K. J.; Hingsgaul, 0. (1991) A simple synthesis of octyl 3,6-di-O-(.alpha.-D-mannopyranosyl)-.beta.-D-manopyranoside and its use as an acceptor for the assay of N-acetylglucosaminetransferase I activity. Glycoconjugate J. 8, 90-94.

Kaur, K. J.; Alton, G.; Hindsgaul, 0. (1991) Use of N-acetylglucosaminyltranserases I and 11 in the preparative synthesis of oligosaccharides. Carbohydr. Res. 210,145-153.

Korner, C.; Knauer, R.; Holzbach, U.; Hanefeld, F.; Lehle, L.; von Figura, K. (1998) Carbohydrate-deficient glycoprotein syndrome type V: deficiency of dolichyl-P-Glc:Man9GlcNAc2-PP-dolichyl glucosyltransferase. Proc Natl Acad Sci U.S.A. 95,13200-13205.

Link, A. J., Hays, L. G., Carmack, E. B., and Yates, J. R., 3rd (1997), "Identifying the major proteome components of *Haemophilus influenzae* type-strain NCTC 8143," Electrophoresis 18:1314-1334.

Link, J. et al. (1999), "Direct analysis of large protein complexes using mass spectrometry," Nat. Biotech. 17:676-682 (July 1999)

Mann, M., and Wilm, M. (1994), "Error-tolerant identification of peptides in sequence databases by peptide sequence tags," Anal. Chem. 66:4390-4399.

McMurry, J. E.; Kocovsky, P. (1984) A method for the palladium-catalyzed allylic oxidation of olefins. Tetrahedron Lett. 25, 4187-4190.

Morris, A. A. M. and Turnbull, D. M. (1994) Curr. Opin. Neurol. 7:535-541.

Neufeld, E. and Muenzer, J. (1995), "The mucopolysaccharidoses" In The Metabolic and Molecular Bases of Inherited Disease, Scriver, C. R. et al. (eds.) McGraw-Hill, New York, pp. 2465-2494.

Oda, Y. et al. (1999), "Accurate quantitation of protein expression and site-specific phosphorylation," Proc. Natl. Acad. Sci. USA 96:6591-6596.

Okada, S. and O'Brien, J. S. (1968) Science 160:10002.

Opiteck, G. J. et al. (1997), "Comprehensive on-line LC/LC/MS of proteins," Anal. Chem. 69:1518-1524.

Paulsen, H.; Meinjohanns, E. (1992) Synthesis of modified oligosaccharides of N-glycoproteins intended for substrate specificity studies of N-acetylglucosaminyltransferases II-V Tetrahedron Lett. 33, 7327-7330.

Paulsen, H.; Meinjohanns, E.; Reck, F.; Brockhausen, I. (1993) Synthese von modifizierten Oligosacchariden der N-Glycoproteine zur Untersuchung der Spezifität der N-Acetylglucosaminyltransferase II. Liebigs Ann. Chem. 721-735.

Pennington, S. R., Wilkins, M. R., Hochstrasser, D. F., and Dunn, M. J. (1997), "Proteome analysis: From protein characterization to biological function," Trends Cell Bio. 7:168-173.

Preiss, J. (1966) GDP-mannose pyrophosphorylase from *Arthrobacter*. In Meth. Enzymol. Vol. VIII, Neufeld, E. F.; Ginsburg, V. Eds; Academic Press: New York 1966, pp. 271-275.

Qin, J. et al. (1997), "A strategy for rapid, high-confidence protein identification," Anal. Chem. 69:3995-4001.

Ronin, C.; Caseti, C.; Bouchilloux, C. (1981) Transfer of glucose in the biosynthesis of thyroid glycoproteins. 1. Inhibition of glucose transfer to oligosaccharide lipids by GDP-mannose. Biochim. Biophys. Acta 674, 48-57.

Ronin, C.; Granier, C.; Caseti, C.; Bouchilloux, S.; Van Rietschoten, J. (1981a) Synthetic substrates for thyroid oligosaccharide transferase. Effects of peptide chain length and modifications in the -Asn-Xaa-Thr- region. Eur. J. Biochem. 118,159-164.

Ronne, H. (1995), "Glucose repression in fungi," Trends Genet. 11:12-17.

Rush, J. S.; Wachter, C. J. (1995) Transmembrane movement of a water-soluble analogue of mannosylphosphoryldolichol is mediated by an endoplasmic reticulum protein. J. Cell. Biol. 130, 529-536.

Schachter, H. (1986) Biosynthetic controls that determine the branching and microheterogeneity of protein-bound oligosaccharides. Biochem. Cell Biol. 64, 163-181.

Scriver, C. R. et al. (1995), The Metabolic and Molecular Bases of Inherited Disease, Scriver, C. R. et al. (eds.) McGraw-Hill, N.Y., pp. 1015-1076.

Sechi, S. and Chait, B. T. (1998), "Modification of cysteine residues by alkylation. A tool in peptide mapping and protein identification," Anal. Chem. 70:5150-5158.

Segal, S. and Berry, G. T. (1995), The Metabolic and Molecular Bases of Inherited Disease, Scriver, C. R. et al. (eds.), McGraw-Hill, N.Y., pp. 967-1000.

Romanowska, A. et al. (1994), "Michael Additions for Synthesis of Neoglycoproteins," Methods Enzymol. Neoconjugates Part A (Synthesis) 242:90-101.

Roth, F. P. et al. (1998), "Finding DNA regulatory motifs within unaligned noncoding sequences clustered by whole-genome mRNA quantitation," Nat. Biotechnol. 16:939-945.

Shalon, D., Smith, S. J., and Brown, P. O. (1996), "A DNA microarray system for analyzing complex DNA samples using two-color fluorescent probe hybridization," Genome Res. 6:639-645.

Shevchenko, A., Jensen, O. N., Podtelejnikov, A. V., Sagliocco, F., Wilm, M., Vorm, O., Mortensen, P., Shevchenko, A., Boucherie, H., and Mann, M. (1996), "Linking genome and proteome by mass spectrometry: large-scale identification of yeast proteins from two dimensional gels," Proc. Natl. Acad. Sci. U.S.A. 93:14440-14445.

Shevchenko, A., Wilm, M., Vorm, O., and Mann, M. (1996), "Mass spectrometric sequencing of proteins silver-stained polyacrylamide gels," Anal. Chem. 68:850-858.

Tan, J.; Dunn, J.; Jaeken, J.; Schachter, H. (1996) Mutations in the MGAT2 gene controlling complex glycan synthesis cause carbohydrate deficient glycoprotein syndrome type II, an autosomal recessive disease with defective brain development. Am. J. Hum. Genet. 59, 810-817.

Velculescu, V. E., Zhang, L., Zhou, W., Vogelstein, J., Basrai, M. A., Bassett, D. E., Jr., Hieter, P., Vogelstein, B., and Kinzler, K. W. (1997), "Characterization of the yeast transcriptome," Cell 88:243-251.

Wilbur, D. S. et al. (1997), "Biotin reagents for antibody pretargeting. Synthesis, radioiodenation and in vitro evaluation of water soluble, biotimidase resistant biotin derivatives," Bioconjugate Chem. 8:572-584.

Yates, J. R. d., Eng, J. K., McCormack, A. L., and Schieltz, D. (1995), "Method to correlate tandem mass spectra of modified peptides to amino acid sequences in the protein database," Anal. Chem. 67:1426-1436.

Variations, modifications, and other implementations of what is described herein will occur to those of ordinary skill in the art without departing from the spirit and scope of the invention as described and claimed herein.

All of the references identified hereinabove, are expressly incorporated herein by reference.

What is claimed is:

1. A reagent for mass spectrometric analysis of proteins comprising a tag molecule, wherein the tag molecule comprises a reactive site for stably associating with a protein, an isotope label, and a biotin compound linked to the tag molecule through a pH or reducing agent sensitive bond, wherein the biotin compound comprises biotin and a 2-[2-(2-iodo-acetylamino)-1,1-dimethyl-ethyldisulfanyl]-3-methyl-butyric acid coupled through a di(2-aminoethyl)ether.

2. The reagent of claim 1, wherein the di(2-aminoethyl) ether comprises one or more ethylene glycol repeat units interposed between the amino residues.

3. The reagent of claim 1, wherein the biotin and the 2-[2-(2-iodo-acetylamino)-1,1-dimethyl-ethyldisulfanyl]-3-methyl-butyric acid are coupled through a linker having the formula: —NH((CH$_2$)$_2$O)$_n$(CH$_2$)$_2$NH—, where n is an integer of from 0 to about 5.

4. A reagent for mass spectrometric analysis of proteins comprising a tag molecule, wherein the tag molecule comprises a reactive site for stably associating with a protein, an isotope label, and a biotin compound linked to the tag molecule through a pH or reducing agent sensitive bond, wherein the tag molecule comprises an anchoring site that forms covalent bonds to a cis hydroxyl pair under selected pH conditions.

5. A reagent for mass spectrometric analysis of proteins comprising a tag molecule, wherein the tag molecule comprises a reactive site for stably associating with a protein, an isotope label, and a biotin compound linked to the tag molecule through a pH or reducing agent sensitive bond, wherein the tag molecule comprises an anchoring site that forms a covalent bond to a serine residue.

6. The reagent according to claim 1 or 5, wherein the reactive site of the tag molecule is stably associated with a protein.

7. The reagent according to claim 1 or 5, wherein the reactive site of the tag molecule is stably associated with a peptide.

8. A reagent for mass spectrometric analysis of proteins comprising a tag molecule, wherein the tag molecule comprises a reactive site for stably associating with a protein, an isotope label, and a biotin compound linked to the tag molecule through a pH or reducing agent sensitive bond, wherein a pH sensitive anchoring group forms a bond with a solid phase under selected pH conditions and wherein the bond is selected from the group consisting of an acyloxyalkyl ether bond, acetal bond, thioacetal bond, aminal bond, imine bond, carbonate bond, ketal bond and disulfide bond.

9. The reagent according to claim 1 or 5, wherein the tag molecule is attached to a solid phase.

10. The reagent according to claim 9, wherein the tag molecule is attached to a solid phase through an avidin/biotin complex.

11. The reagent according to claim 1 or 5, wherein the tag molecule is attached to a solid phase through an avidin/biotin complex.

12. The reagent according to claim 1 or 5, wherein the tag molecule is about 175-300 daltons.

13. The reagent according to claim 2, wherein the isotope is covalently bound to the tag molecule.

14. The reagent according to claim 1 or 5, wherein the reactive site forms stable associations with a modified residue of a protein.

15. The reagent according to claim 14, wherein the modified residue is glycosylated, methylated, acylated, phosphorylated, ubiquinated, farnesylated, or ribosylated.

16. A composition comprising a pair of tag molecules according to claim 1 or 5, wherein each member of the pair is identical except for the mass of the isotope attached thereto.

17. The composition according to claim 16, wherein one member of the pair comprises a heavy isotope and the other member of the pair comprises the corresponding light form of the isotope.

18. A compound having the formula

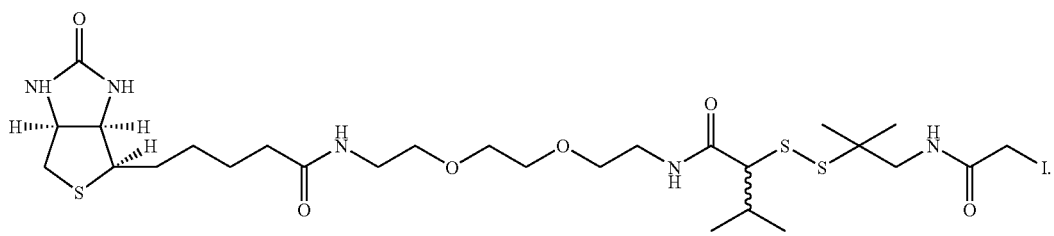

19. The compound of claim 18 wherein the group coupled to the biotin compound though the disulfide bond is labeled with C$^{13}$ to have a molecular weight that is greater by six.

* * * * *

UNITED STATES PATENT AND TRADEMARK OFFICE
CERTIFICATE OF CORRECTION

PATENT NO. : 7,332,613 B2  
APPLICATION NO. : 10/863589  
DATED : February 19, 2008  
INVENTOR(S) : Gygi et al.

Page 1 of 1

It is certified that error appears in the above-identified patent and that said Letters Patent is hereby corrected as shown below:

In the Specification

Delete the paragraph beginning at Column 1, Line number 13 and replace it with the following paragraph:
This invention was made with government support under HG000041 awarded by the National Institutes of Health. The government has certain rights in the invention.

Signed and Sealed this
Fourteenth Day of January, 2025

Derrick Brent
*Acting Director of the United States Patent and Trademark Office*